United States Patent [19]
Dassel et al.

[11] Patent Number: 5,883,292
[45] Date of Patent: Mar. 16, 1999

[54] REACTION CONTROL BY REGULATING INTERNAL CONDENSATION INSIDE A REACTOR

[75] Inventors: Mark William Dassel, Indianola, Wash.; Eustathios Vassiliou, Newark, Del.

[73] Assignee: Twenty-First Century Research Corporation, Newark, Del.

[21] Appl. No.: 587,967

[22] Filed: Jan. 17, 1996

[51] Int. Cl.$^6$ ........................................ C07C 51/16
[52] U.S. Cl. .................. 562/413; 562/509; 562/512.4; 562/523; 562/542; 562/543; 562/549
[58] Field of Search .................. 562/413, 509, 562/512.4, 523, 542, 543, 549

[56] References Cited

U.S. PATENT DOCUMENTS

| | | |
|---|---|---|
| 1,121,532 | 12/1914 | Newberry . |
| 2,014,044 | 9/1935 | Haswell ........................................ 75/17 |
| 2,301,240 | 11/1942 | Baumann ................................ 183/115 |
| 2,980,523 | 4/1961 | Dille et al. ................................ 48/215 |
| 3,290,369 | 12/1966 | Bonfield et al. ........................ 260/537 |
| 3,530,185 | 9/1970 | Pugi ........................................ 260/586 |
| 3,613,333 | 10/1971 | Gardenier ................................ 55/89 |
| 3,677,696 | 7/1972 | Bryk et al. ................................ 23/2 |
| 3,928,005 | 12/1975 | Laslo ........................................ 55/73 |
| 3,987,100 | 10/1976 | Barnette et al. ........................ 260/586 |
| 3,987,808 | 10/1976 | Carbonell et al. ........................ 137/3 |
| 4,039,304 | 8/1977 | Bechthold et al. ........................ 55/10 |
| 4,065,527 | 12/1977 | Graber ................................ 261/79 A |
| 4,308,037 | 12/1981 | Meissner et al. ........................ 55/10 |
| 4,361,965 | 12/1982 | Goumondy et al. ........................ 34/57 |
| 4,370,304 | 1/1983 | Hendriks et al. ........................ 422/224 |
| 4,419,184 | 12/1983 | Backlund ................................ 162/49 |
| 4,423,018 | 12/1983 | Lester, Jr. et al. ........................ 423/243 |
| 4,543,399 | 9/1985 | Jenkins, III et al. ........................ 526/70 |
| 4,588,790 | 5/1986 | Jenkins, III et al. ........................ 526/70 |
| 5,061,453 | 10/1991 | Krippl et al. ........................ 422/106 |
| 5,123,936 | 6/1992 | Stone et al. ................................ 55/8 |
| 5,170,727 | 12/1992 | Nielsen ................................ 110/346 |
| 5,221,800 | 6/1993 | Park et al. ................................ 562/543 |
| 5,244,603 | 9/1993 | Davis ........................................ 261/87 |
| 5,270,019 | 12/1993 | Melton et al. ........................ 422/234 |
| 5,312,567 | 5/1994 | Kozma et al. ........................ 261/87 |
| 5,321,157 | 6/1994 | Kollar ................................ 562/543 |
| 5,396,850 | 3/1995 | Conochie et al. ........................ 110/346 |
| 5,399,750 | 3/1995 | Brun et al. ................................ 562/553 |
| 5,463,119 | 10/1995 | Kollar ................................ 562/543 |

FOREIGN PATENT DOCUMENTS

| | | |
|---|---|---|
| 0439007A2 | 7/1991 | European Pat. Off. . |
| 0751105A2 | 1/1997 | European Pat. Off. . |
| 415172 | 8/1934 | United Kingdom . |
| 738808 | 10/1955 | United Kingdom . |

*Primary Examiner*—Paul J. Killos
*Attorney, Agent, or Firm*—Seed and Berry LLP

[57] ABSTRACT

Methods and apparatuses for controlling exothermic reactions involving a first reactant contained in a liquid and a second reactant in a gas to form a reaction product by atomizing the liquid in an environment of a gas and removing heat of reaction by condensing vapors of the liquid in a reaction chamber. Preferably, the condensation takes place on a simultaneously atomized second liquid of lower temperature than the atomized liquid containing the first reactant. The compositions of the two liquids are preferably similar. This invention provides waste minimization and considerable environmental improvement.

34 Claims, 5 Drawing Sheets

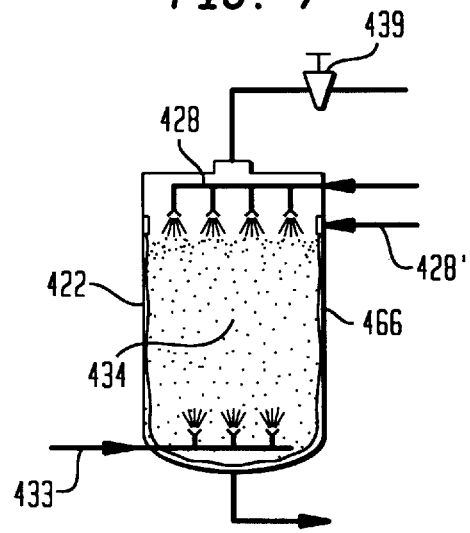
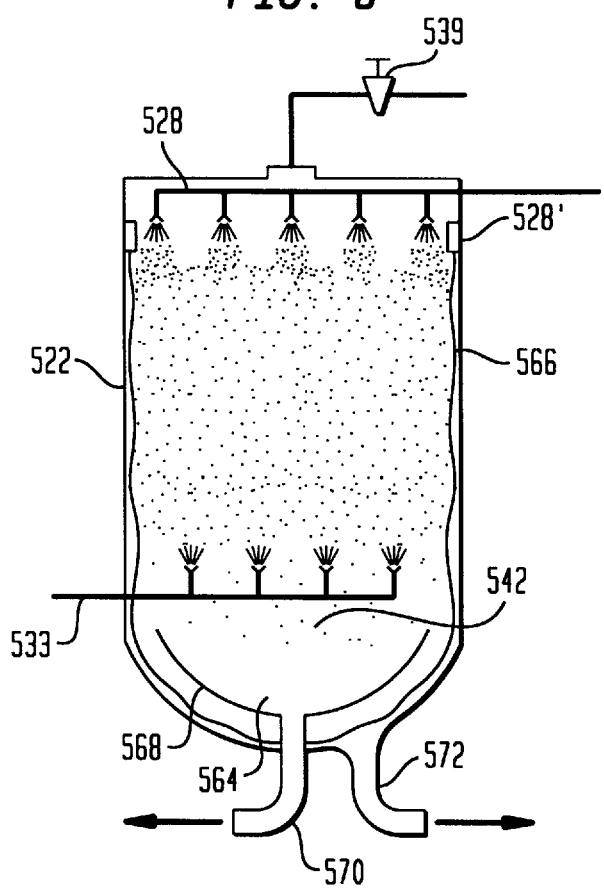

REACTION CONTROL BY REGULATING INTERNAL CONDENSATION INSIDE A REACTOR

FIELD OF THE INVENTION

This invention relates to methods and devices for making reaction products, wherein a first reactant incorporated in an atomized liquid reacts with a gas containing a second reactant, under controlled condensation and temperature conditions. It provides waste minimization and considerable environmental improvement.

BACKGROUND OF THE INVENTION

Reactions where a first reactant, dissolved in a liquid, reacts with a second reactant contained in a gas under increased surface area conditions are known to the art. Such reactions are carried out in devices as scrubbers, burners, reaction vessels, and the like, for example.

Atomization of liquids into a gaseous atmosphere is one of the above mentioned techniques described in the art. The atomization techniques for conducting reactions, disclosed in the art so far, are rather crude and lack innovative features for controlling such reactions with respect to: desired reaction product if the reaction product is an intermediate, yield in reaction product, conversion and conversion rate, temperature profiles in the reaction zone, average droplet size or diameter, evaporation rates, and the like. Actually in most, if not all, cases, the reaction product is substantially the final product expected under the crude overall conditions of the reaction. For example, in the case of a burner, where a fuel is atomized into an atmosphere of an oxygen-containing gas (such as air for example), the final product of reaction is carbon dioxide, with desired minimization of carbon monoxide and nitrogen oxides as much as possible. In another example, a scrubber for removing acidic compounds from a gas may use an atomized liquid containing alkali or alkaline earth compounds which react with the acidic compounds in the gas to form the corresponding salts. In still another example, ammonia and phosphoric acid react under atomization conditions to form ammonium orthophosphate, which is a final reaction product.

On the other hand, reactions which are geared to produce intermediate products, especially in the case of oxidations, are not run under atomization conditions, since atomization promotes complete reactions to a final product. For example, oxidation of cyclohexane to adipic acid, or oxidation of p-xylene to terephthalic acid, have not been reported to be conducted under atomization conditions, and there is no incentive in the art to do so, since burning of cyclohexane to carbon dioxide has been expected to take place under such conditions. However, the inventors have discovered that in the presence of unexpected intricate critical controls and requirements of the instant invention, intermediate reaction or oxidation products, such as adipic acid, phthalic acid, isophthalic acid and terephthalic acid, for example, may be advantageously obtained under atomization conditions.

The following references, among others, describe processes conducted in intermixing liquid with gaseous materials, mostly under increased surface area conditions.

U.S. Pat. No. 5,399,750 (Brun et al.) discloses methods for preparing maleamic acid (aminomaleic acid) by reacting gaseous ammonia with molten maleic anhydride under reactant contact conditions of high surface area, for example reacting said gaseous $NH_3$ with a thin film of said molten maleic anhydride or with said molten maleic anhydride in a state of vigorous agitation.

U.S. Pat. No. 5,396,850 (Connote et al.) discloses a method of destroying organic waste in a bath of molten metal and slag contained in a vessel. The method comprises injecting organic waste into the bath to form a primary reaction zone in which the organic waste is thermally cracked and the products of the thermal cracking which are not absorbed into the bath are released into the space above the surface of the bath. The method further comprises injecting an oxygen-containing gas toward the surface of the bath to form a secondary reaction zone in the space above the surface of the bath in which the oxidizable materials in the products from the primary reaction zone are completely oxidized and the heat released by such oxidation is transferred to the bath. In order to facilitate efficient heat transfer from the second reaction zone to the bath, the method further comprises injecting an inert or other suitable gas into the bath to cause molten metal and slag to be ejected upwardly from the bath into the secondary reaction zone.

U.S. Pat. No. 5,312,567 (Kozma et al.) discloses a complex mixing system with stages consisting of propeller mixers of high diameter ratio, where the blades are provided with flow modifying elements, whereby the energy proportions spent on dispersion of the amount of gas injected into the reactor, homogenization of the multi-phase mixtures, suspension of solid particles, etc. and the properties corresponding to the rheological properties of the gas-liquid mixtures and to the special requirements of the processes can be ensured even in extreme cases. Open channels opposite to the direction of rotation are on the blades of the dispersing stage of the propeller mixers fixed to a common shaft, where the channels are interconnected with gas inlet. The angle of incidence of a certain part of the blades of mixing stages used for homogenization and suspension is of opposite direction and the length is shorter and/or the angle of incidence is smaller than those of the other blades. Baffle bars are on the trailing end of the blades on a certain part of the propeller mixers used similarly for homogenization and suspension, and/or auxiliary blades at an angle of max. 20° to the blade wings are arranged above or below the trailing end of the blades.

U.S. Pat. No. 5,244,603 (Davis) discloses a gas-liquid mixing system which employs an impeller/draft tube assembly submerged in liquid. Hollow eductor tubes affixed to the impeller drive shaft are used to flow gas from an overhead gas space to the liquid in the vicinity of the assembly. The positioning and size of the eductor tubes are such as to maximize the desired gas-liquid mixing and reaction rate.

U.S. Pat. No. 5,270,019 (Melton et al.) discloses an elongated, generally vertically extending concurrent reactor vessel for the production of hypochlorous acid by the mixing and reaction of a liquid alkali metal hydroxide and a gaseous halogen, wherein an atomizer is mounted near the top of the reactor vessel to atomize the liquid alkali metal hydroxide into droplets in the vessel. The vessel has a spraying and reaction zone immediately beneath the atomizer and a drying zone beneath the spraying and reaction zone to produce a gaseous hypochlorous acid and a substantially dry solid salt by-product.

U.S. Pat. No. 5,170,727 (Nielsen) discloses a process and apparatus in which supercritical fluids are used as viscosity reduction diluents for liquid fuels or waste materials which are then spray atomized into a combustion chamber. The addition of supercritical fluid to the liquid fuel and/or waste material allows viscous petroleum fractions and other liquids such as viscous waste materials that are too viscous to be atomized (or to be atomized well) to now be atomized by this invention by achieving viscosity reduction and allowing the fuel to produce a combustible spray and improved combustion efficiency. Moreover, the present invention also allows liquid fuels that have suitable viscosities to be better utilized as a fuel by achieving further viscosity reduction that improves atomization still further by reducing droplet size which enhances evaporation of the fuel from the droplets.

U.S. Pat. No. 5,123,936 (Stone et al.) discloses a process and apparatus for removing fine particulate matter and vapors from a process exhaust air stream, and particularly those emitted during post-production curing or post-treatment of foamed plastics, such as polyurethane foam, in which the exhaust air stream is passed through a transfer duct into which is introduced a water spray in the form of a mist of fine droplets in an amount which exceeds the saturation point; thereafter the exhaust air stream is introduced into a filter chamber having a cross-sectional area that is substantially greater than that of the transfer duct, and the exhaust air stream passes through at least one, and preferably a plurality of high surface area filters, whereby a portion of the water is removed from the exhaust air stream and collected in the filter chamber prior to the discharge of the exhaust air stream into the environment.

U.S. Pat. No. 5,061,453 (Krippl et al.) discloses an apparatus for continuously charging a liquid reactant with a gas. The gas is dispersed in the reactant through a hollow stirrer in a gassing tank. The quantity of gas introduced per unit time is kept constant.

U.S. Pat. No. 4,423,018 (Lester, Jr. et al.) discloses a process according to which a by-product stream from the production of adipic acid from cyclohexane, containing glutaric acid, succinic acid and adipic acid, is employed as a buffer in lime or limestone flue gas scrubbing for the removal of sulfur dioxide from combustion gases.

U.S. Pat. No. 4,370,304 (Hendriks et al.) discloses methods by which ammonium orthophosphate products are prepared by reacting ammonia and phosphoric acid together at high speed under vigorous mixing conditions by spraying the reactants through a two-phase, dual coaxial mixer/sprayer and separately controlling the supply and axial outflow rate of the phosphoric acid at 1 to 10 m/sec. and the outflow rate of ammonia at 200 to 1000 m/sec. (N.T.P.). Thorough mixing and a homogenous product is obtained by directing the outflow spray into a coaxial cylindrical reaction chamber of a specified size with respect to the diameter of the outermost duct of the sprayer/mixer. The product may be granulated on a moving bed of granules and adjusted in respect of the $NH_3$ to $H_3PO_4$ content by changing the concentration of the phosphoric acid and/or supplying additional ammonia to the granulation bed.

U.S. Pat. No. 4,361,965 (Goumondy et al.) discloses a device for atomizing a reaction mixture, said device enabling the reaction mixture to be atomized in a reactor with the aid of at least a first gas and an atomizing nozzle. This device further comprises a supply of a second hot gas at the top of the atomizing device, serving to dry the atomized mixture, a supply of a third gas and means for distributing this third gas comprising an annular space of adjustable width and adapted to distribute in the reactor said third gas in the form of a ring along the inner wall of the reactor, so as to avoid any contact between the reaction mixture and said wall. The invention is applicable to the atomization of a reaction mixture.

U.S. Pat. No. 4,308,037 (Meissner et al.) discloses methods according to which high temperature thermal exchange between molten liquid and a gas stream is effected by generating in a confined flow passageway a plurality of droplets of molten liquid and by passing a stream through the passageway in heat exchange relationship with the droplets. The droplets are recovered and adjusted to a predetermined temperature by means of thermal exchange with an external source for recycle. The process provides for removal of undesired solid, liquid or gaseous components.

U.S. Pat. No. 4,065,527 (Graber) discloses an apparatus and a method for handling a gas and a liquid in a manner to cause a specific interaction between them. The gas is placed into circulation to cause it to make a liquid circulate in a vortex fashion to present a liquid curtain. The gas is then passed through the liquid curtain by angled vanes to cause the interaction between the two fluids, such as the heating of the liquid, scrubbing of the gas, adding a chemical to the liquid and the like. The vanes are spaced apart and project inwardly from the inner periphery of an annular support so that the circulating liquid readily moves into the spaces between the vanes to create the liquid curtain. A number of embodiments of the invention are disclosed.

U.S. Pat. No. 4,039,304 (Bechthold et al.) discloses methods according to which waste gas is contacted with a solution of a salt from a pollutant of the gas. This solution is obtained from another stage of the process used for cleaning or purifying the gas. The resulting mixture of gas and solution is subjected to vaporization so as to obtain a dry gaseous substance constituted by the waste gas and the evaporated solvent for the salt. The gaseous substance thus formed contains crystals of the salt as well as the pollutant present in the original waste gas. The salt crystals and other solid particles are removed from the gaseous substance in the form of a dry solids mixture. The gaseous substance is subsequently mixed with an absorption fluid such as an ammonia solution in order to wash out and redissolve any salt crystals which may remain in the gaseous substance and in order to remove the pollutant present in the original waste gas from the gaseous substance. The pollutant and the redissolved salt crystals form a salt solution together with the absorption fluid and it is this salt solution which is brought into contact with the waste gas. The gaseous substance is exhausted to the atmosphere after being mixed with the absorption fluid.

U.S. Pat. No. 3,928,005 (Laslo) discloses a method and apparatus for treating gaseous pollutants such as sulfur dioxide in a gas stream which includes a wet scrubber wherein a compressed gas is used to atomize the scrubbing liquid and a nozzle and the compressed gas direct the atomized liquid countercurrent to the flow of gas to be cleaned. The method and apparatus includes pneumatically conveying to the nozzle a material such as a solid particulate material which reacts with or modifies the pollutant to be removed or altered. The gas used for atomizing the scrubbing liquid is also used as a transport vehicle for the solid particulate material. In the case of sulfur oxides, the material may be pulverized limestone.

U.S. Pat. No. 3,677,696 (Helsinki et al) discloses a method according to which, the concentration of circulating sulfuric acid is adjusted to 80–98% by weight and used to wash hot gases containing mercury. The temperature of the acid is maintained between 70°–250° C., and the solid material separating from the circulating wash solution is recovered.

U.S. Pat. No. 3,613,333 (Gardenier) discloses a process and apparatus for removing contaminants from and pumping a gas stream comprising indirectly heat exchanging the gas and a liquid, introducing the liquid under conditions of elevated temperature and pressure in vaporized and atomized form into the gas, mixing same thereby entrapping the contaminants, and separating clean gas from the atomized liquid containing the contaminants.

U.S. Pat. No. 2,980,523 (Dille et al.) discloses a process for the production of carbon monoxide and hydrogen from carbonaceous fuels by reaction with oxygen. In one of its more specific aspects it is directed to a method of separating carbonaceous solid entrained in the gaseous products of reaction of carbonaceous fuels and oxygen wherein said products are contacted with a limited amount of liquid hydrocarbon and thereafter scrubbed with water, and said carbonaceous solid is decanted from said clarified water.

U.S. Pat. No. 2,301,240 (Baumann et al.) discloses an improved process for removing impurities from acetylene gas which has been prepared by thermal or electrical methods by washing with organic liquids, as for example oils or tars.

U.S. Pat. No. 2,014,044 (Haswell) discloses an improved method for treating gas and aims to provide for the conservation of the sensible heat of such gas.

U.S. Pat. No. 1,121,532 (Newberry) discloses a process of recovering alkalis from flue-gases.

Currently, oxidation reactions for the production of organic acids, including but not limited to adipic acid, are conducted in a liquid phase reactor with reactant gas sparging. The reactant gas in these cases is typically air, but may also be oxygen. Sufficient reactant gas, with or without non-reactive diluents (e.g., nitrogen), is sparged—at relatively high rate—so that the liquid reaction medium is aerated to maximum capacity (typically 15–25% aeration). The relatively high sparging rates of reactant containing gas feed (hereinafter referred to as "reactant gas"), associated with this conventional approach, have several drawbacks:

Costly reactant gas feed compressors are required to compress makeup reactant gas for sparging. These are expensive to install and operate (high electric or steam consumption), and have many utility problems resulting in excessive plant downtime.

The required high gas rate makes it extremely difficult to control oxygen content in the reactor at low concentrations (due to the high reactor gas turnover rate).

The required high gas rate makes it extremely difficult to control reaction temperature at low production rates (i.e., high turndown rate) for a given sized reactor system. This occurs because the gas used for sparging removes energy from the reaction system by volatilizing reaction liquid and liquid solvent—this volatilization effect is quite significant at the relatively high temperatures commonly associated with and required for oxidation reactions. Unless carefully balanced by an exothermic heat of reaction, this volatilization will act to substantially lower the temperature of the liquid content of the reactor. Thus, a properly sparged system can be designed for good temperature control at medium to high production rates, but will suffer temperature loss and loss of temperature control at significant turndown rate.

High reactant gas feed rate results in relatively high reactor non-condensible off-gas rate. Non-condensible off-gases must either be totally purged to atmosphere, or—if oxygen content is high-partially purged and partially recycled to the reactor. The use of air as a reactant gas feed has drawbacks because it results in high rate of purge to the atmosphere—this is undesirable because this purge must first be cleaned in very expensive off-gas cleanup facilities in order to meet ever more stringent environmental requirements. The use of oxygen-only gas feed to the reactor may be undesirable because high sparging requirements result in low oxygen conversion in the reactor; low conversion results in high oxygen concentration within the reactor; and high oxygen concentration within the reactor may result in excessive over-oxidation of liquid reactants and liquid solvents with attendant high chemical yield loss (i.e., burning these to carbon monoxide and carbon dioxide). If the oxygen in the reactor is diluted with recycle nitrogen or gaseous-recycle inerts, then both high recompression investment and costs, and recompression utility problems are introduced.

The current technology also suffers from a relatively low ratio of gas-liquid surface area to liquid reaction mass. The presently available art does not maximize this ratio. In contrast, the present invention maximizes said ratio in order:

to increase reaction rate by increasing the mass transfer rate of gaseous reactants to liquid reaction sites; and so as to enable economic operation at relatively low concentration of a second reactant, such as an oxidant for example, in the gas phase.

Operating at lower oxygen concentration with acceptable conversion rates in the reactor improves yield by reducing over-oxidations, and eliminates safety (explosion) problems associated with operation in the explosive oxygen/fuel envelope. In the current technology, reducing oxygen content below traditional levels would result in a non-economic reduction in reaction rate. However, a significant increase in the aforementioned ratio—relative to current levels—would offset this rate reduction thereby enabling economic operation at reduced oxygen concentration in the reactor.

Another problem with the current technology is the sometimes formation of large agglomerations of insoluble oxidation products in the reactor. These can build up on reactor walls resulting in decreased available reaction volume, and in unwanted by-product formation due to over-exposure of said accretions to reaction conditions (e.g., high temperature) in oxygen-starved micro-reactor environments. These can also form large diameter, heavy solids in the reactor which can result in damage to expensive reactor agitator shafts and agitator seals resulting in costly repairs and high utility wear-problems. Finally, the current technology often requires expensive agitation shafts and seals capable of withstanding corrosive chemical attack and containing high system pressures.

Substituting gas-phase reaction systems for liquid-phase reactors introduces new problems, chief among which is the difficulty of identifying a cost-effective, efficient, non-plugging, long-lived catalyst system. Liquid-phase catalyst systems are well-developed and well-understood. Unfortunately, these are non-volatile. Using a non-volatile catalyst in a gas-phase reaction system must necessarily often be subject to severe plugging problems as most organic acids resulting from oxidation reactions are non-volatile solids—unless dissolved in a liquid reaction medium.

There is a plethora of references dealing with oxidation of organic compounds to produce acids, such as, for example, adipic acid.

The following references, among the plethora of others, may be considered as representative of oxidation processes relative to the preparation of diacids.

U.S. Pat. No. 5,321,157 (Kollar) discloses a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
  (a) at least one saturated cycloaliphatic hydrocarbon having from 5 to 8 ring carbon atoms in the liquid phase and
  (b) an excess of oxygen gas or an oxygen containing gas mixture in the presence of
  (c) less than 1.5% moles of a solvent per mole of cycloaliphatic hydrocarbon (a), wherein said solvent comprises an organic acid containing only primary and/or secondary hydrogen atoms and
  (d) at least about 0.002 mole per 1000 grams of reaction mixture of a polyvalent heavy metal catalyst; and
(2) isolating the C5–C8 aliphatic dibasic acid.

U.S. Pat. No. 5,463,119 (Kollar) discloses a process for the preparation of $C_5$–$C_8$ aliphatic dibasic acids, similar to the one described in U.S. Pat. No. 5,321,157, with the main difference that after removing the adipic acid, the remaining matter is recirculated.

U.S. Pat. No. 5,221,800 (Park et al.) discloses a process for the manufacture of adipic acid, according to which cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to 150° C., at an oxygen partial pressure of about 50 to about 420 pounds per square inch absolute.

The following references, among others, describe oxidation processes conducted in multi-stage and multi-plate systems.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,530,185 (Pugi) describes a process for manufacturing precursors of adipic acid by oxidation of an oxygen containing inert gas which process is conducted in at least three successive oxidation stages by passing a stream of liquid cyclohexane maintained at a temperature in the range of 140° to 200° C., and a pressure in the range of 50–350 psig through each successive oxidation stage in an amount such that substantially all the oxygen introduced into each stage is consumed in that stage thereafter causing the residual inert gases to pass countercurrent into the stream of liquid during the passage of the stream through said stages.

None of the above references, or any other references known to the inventors disclose, suggest or imply, singly or in combination, devices for conducting reactions under atomization conditions subject to the intricate and critical controls and requirements of the instant invention as described and claimed.

SUMMARY OF THE INVENTION

As aforementioned, the present invention relates to methods and devices for making reaction products, wherein a first reactant incorporated in an atomized liquid reacts with a gas containing a second reactant, under controlled condensation and temperature conditions. More particularly, it pertains to a method of making a reaction product in a reaction zone in an exothermic reaction from a first liquid containing a first reactant and a gas containing a second reactant, the method comprising the steps of:

atomizing the first liquid to form a plurality of first droplets in the gas at a first flow rate, at a first atomization temperature, and at a reaction pressure;

reacting at least partially the first reactant with the second reactant to form the reaction product and release heat;

evaporating at least part of the first liquid, thereby removing at least a portion of the released heat; and restricting the portion of removed heat within predetermined limits by causing controlled condensation within the reaction zone.

The present invention also pertains to a method of making a reaction product in an exothermic reaction from a first liquid containing a first reactant and a gas containing a second reactant, the method comprising the steps of:

dividing the first liquid into a first stream and to a second stream;

causing the first stream to have a first atomization temperature and the second stream to have a second atomization temperature lower than the first atomization temperature;

atomizing the first stream to form a plurality of first droplets in the gas at a first flow rate and at the first atomization temperature;

atomizing the second stream to form a plurality of second droplets in the gas at a second flow rate and at the second atomization temperature;

reacting at least partially the first reactant in the first droplets with the second reactant to form the reaction product and release heat; and maintaining first droplet temperature within predetermined limits by
  evaporation of at least part of the first liquid from the first droplets, and
  condensation of at least part of the evaporated first liquid on the second droplets.

Further, the instant invention is related to a method of making a reaction product in an exothermic reaction from a first liquid containing a first reactant and a gas containing a second reactant, the method comprising the steps of:

dividing the first liquid into a first stream and to a second stream;

causing the first stream to have a first atomization temperature and the second stream to have a second atomization temperature lower than the first atomization temperature;

atomizing the first stream to form a plurality of first droplets in the gas at a first flow rate and at the first atomization temperature;

atomizing the second stream to form a plurality of second droplets in the gas at a second flow rate and at the second atomization temperature;

reacting at least partially the first reactant in the first droplets with the second reactant to form the reaction product and release heat; and maintaining first droplet temperature within predetermined limits by transferring heat from the first droplets to the second droplets.

The controlled condensation is preferably caused by a second liquid atomized within the reaction zone. The second liquid may contain volatiles at a desired content, the volatiles having a desired volatility. The second liquid may enter the reaction zone under a condition selected from a group consisting of a second flow rate, a second atomization temperature, and a combination thereof, the second atomization temperature being lower than the first atomization temperature.

The first liquid may also contain volatiles at a desired content, the volatiles having a desired volatility.

The condensation rate may be at least partially controlled by one parameter selected from a group consisting of (a) temperature difference between the first and the second atomization temperature, (b) flow rate difference between the first and the second flow rate (c) the volatiles content of the first liquid, (d) the volatiles content of the second liquid, (e) the volatility of the first or second volatiles, and (f) a combination thereof. The condensation rate may also be controlled by changing the reaction pressure.

It is preferable that, if the first liquid comprises a first set of ingredients, and the second liquid comprises a second set of ingredients, the first set and the second set have at least one common ingredient. It is more preferable that the first set and the second set comprise substantially the same ingredients, and even more preferable that the substantially same ingredients are substantially under the same proportions.

The controlled condensation may be caused by a solid or liquid surface within the reaction zone or by a solid or liquid surface in the periphery of the reaction zone, or any combination thereof.

Provisions may be made so that condensed material is at least partially separated from reacted material.

It is preferable that the total amount of second reactant fed to the reaction zone is in a range corresponding to stoichiometric to two times stoichiometric with respect to the total amount of first reactant fed to the reaction zone.

The present invention also pertains to methods as aforedescribed, wherein the first reactant comprises a compound selected from a group consisting of cyclohexane, cyclohexanone, cyclohexanol, cyclohexylhydroperoxide, o-xylene, p-xylene, m-xylene, a mixture of at least two of cyclohexane, cyclohexanone, cyclohexanol, and cyclohexylhydroperoxide, and a mixture of at least two of o-xylene, p-xylene, and m-xylene;

the second reactant comprises oxygen; and the reaction product comprises a compound selected from a group consisting of cyclohexanone, cyclohexanol, cyclohexylhydroperoxide, adipic acid, phthalic acid, isophthalic acid, terephthalic acid, a mixture of at least two of cyclohexanone, cyclohexanol, and cyclohexylhydroperoxide, and a mixture of at least two of phthalic acid, isophthalic acid, and terephthalic acid.

The present invention relates also to a method, wherein the first liquid contains a catalyst at a desired concentration, the first and second reactants are characterized by desired concentrations, the exothermic reaction is characterized by a conversion of the first reactant to reaction product, the exothermic reaction takes place in a reaction zone, the first droplets have a path within said reaction zone, said first droplets have a temperature as function of their path through the reaction zone, wherein said conversion is controlled by a parameter selected from a group consisting of:

changing the first atomization temperature;
changing the second atomization temperature;
changing the catalyst concentration;
changing the first reactant concentration in the first liquid;
changing the volatiles content in the first liquid;
changing the volatiles content in the second liquid;
changing the second reactant concentration;
changing the droplet size of the first liquid; and
a combination thereof; and
wherein said first droplet temperature is controlled by a parameter selected from a group consisting of:
changing the first atomization temperature;
changing the second atomization temperature;
changing the catalyst concentration;
changing the first reactant concentration;
changing the volatiles content in the first liquid;
changing the volatiles content in the second liquid;
changing the second reactant concentration;
changing the droplet size of the first liquid; and
a combination thereof.

This invention also pertains to a method, wherein the average droplet size of the second liquid is maintained at least adequately smaller than the average droplet size of the first liquid in a manner to decrease the probabilities of first droplets to collide with second droplets as compared to such probabilities when the average size of the second droplets is substantially the same as the average size of the first droplets.

Further, the instant invention pertains to a method, wherein the reaction product comprises a compound selected from a group consisting of adipic acid, phthalic acid, isophthalic acid, and terephthalic acid, and the method further comprises a step of reacting said reaction product with a third reactant selected from a group consisting of a polyol, a polyamine, and a polyamide in a manner to form a polymer of a polyester, or a polyamide, or a (polyimide and/or polyamideimide), respectively.

The method may further comprise a step of spinning the polymer into fibers.

The present invention also pertains to an apparatus for making a reaction product in an exothermic reaction from a first liquid containing a first reactant and a gas containing a second reactant, comprising a reaction chamber;

a first atomizer in the reaction chamber for atomizing the first liquid at a first flow rate, a first atomization temperature, and at a reaction pressure;

condensing means within the reaction chamber for condensing vapors; and control means for maintaining first droplet temperature lower than a predetermined value by transferring heat from the first droplets to the condensing means.

The condensing means may comprise a second atomizer for atomizing a second liquid at a second flow rate, and at a second atomization temperature. It is preferable that at least one of the first and the second atomizer is adapted to conduct interrupted atomization at desired intervals.

The apparatus may further comprise one or more of:

means for measuring the temperature of the droplets within the reaction chamber;

means for recycling the first liquid in the reaction chamber;

a divider for dividing the recycled first liquid into a first stream and a second stream, the first stream being directed to the first atomizer and the second stream being directed to the second atomizer;

heating and/or cooling means (temperature controlling means) for bringing the first stream to the first atomization temperature and the second stream to the second atomization temperature;

an arrangement, wherein the control means are adapted to maintain the first droplet temperature within predetermined limits by regulating the flow rates and atomization temperatures of the first and the second liquids;

an arrangement wherein the control means are adapted to utilize data concerning temperature profiles in the reaction chamber in order to regulate the flow rates and atomization temperatures of the first and the second liquids; and means for feeding a total amount of second reactant in the reaction zone, the total amount of second reactant being in a range corresponding to stoichiometric to two times stoichiometric with respect to a total amount of first reactant fed to the reaction zone.

BRIEF DESCRIPTION OF THE DRAWING

The reader's understanding of this invention will be enhanced by reference to the following detailed description taken in combination with the drawing figures, wherein:

FIG. 7 illustrates schematically still another preferred embodiment of the present invention, wherein the condensation takes place on a liquid surface surrounding the reaction zone.

FIG. 8 illustrates schematically still another preferred embodiment of the present invention, wherein the condensation takes place on a liquid surface surrounding the reaction zone, and wherein condensed material is at least partially separated from reacted material.

DETAILED DESCRIPTION OF THE INVENTION

Figure 1:
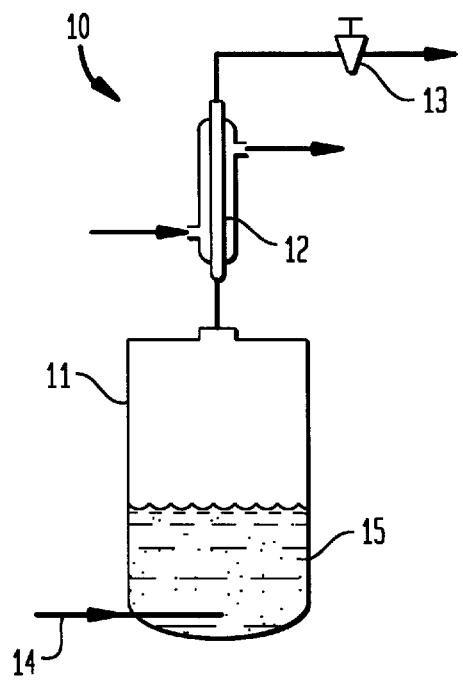
FIG. 1 illustrates schematically a conventional reactor using internal condensation.

As aforementioned, the present invention relates to methods and devices for making reaction products, and preferably intermediate oxidation products, wherein a first reactant incorporated in an atomized liquid reacts with a gas containing a second reactant, which may preferably be an oxidant, under controlled conditions. The term "intermediate oxidation product", as aforementioned, signifies that the oxidation stops before substantially oxidizing the first reactant to carbon monoxide, carbon dioxide, or mixtures thereof. According to the present invention, the atomization conditions are subject to intricate critical controls and requirements as described and claimed hereinbelow.

According to the present invention, conversion refers to conversion of a reactant to a reaction product. Thus conversion, at any point during a reaction, is defined as the percentage ratio of moles of reaction product formed during the reaction to the total moles of reactant in the feedstock, multiplied by the reciprocal of the number of moles of reaction product produced theoretically when one mole of reactant is completely converted to said reaction product.

Transient conversion is the conversion taking place from the point that the first liquid is atomized to form first droplets to the point just before the first droplets coalesce to a mass of liquid, as described hereinwith. This occurs in just one cycle of droplet formation and droplet coalescence.

Reactions which are geared to produce intermediate products, especially in the case of oxidations, have not been run under atomization conditions so far, since atomization promotes complete reactions to a final product. For example, oxidation of cyclohexane to adipic acid, or oxidation of p-xylene to terephthalic acid, have not been reported to be conducted under atomization conditions, and there is no incentive in the art to do so, since burning of cyclohexane to carbon dioxide has been expected to take place under such conditions. However, the inventors have discovered that in the presence of unexpected intricate critical controls and requirements of the instant invention, intermediate reaction or oxidation products, such as adipic acid, phthalic acid, isophthalic acid and terephthalic acid, for example, may be advantageously obtained under atomization conditions.

The present invention enables economic oxidation reactions at improved yield with reduced compression costs and investment, using proven catalyst systems, with reduced off-gas waste-stream discharge to the atmosphere, with reduced off-gas cleanup investment and costs, without solids plugging or buildup problems, with high utility, high conversion rates, and with reduced oxygen concentrations in the reaction chamber.

The ability to operate at lower oxygen concentration, made possible by this invention, with acceptable conversion rates in the reactor improves yield by reducing over-oxidations, and may eliminate safety (explosion) problems associated with operation in the explosive oxygen/fuel envelope by operating in the non-explosive oxygen/fuel envelope. In the current technology, reducing oxygen content below traditional levels would result in a non-economic reduction in reaction rate. In this invention, however, a significant increase in the ratio of gas-liquid interfacial area to liquid reaction mass—relative to current levels—offsets this rate reduction, thereby enabling economic operation at reduced oxygen concentration in the reactor.

Yield improvements and/or operation parameters according to this invention result in waste minimization and considerable environmental improvement, which is a very important for the protection of the environment.

Some of the key elements, which may be present singly or in any combination thereof, in the embodiments of the present invention, are:

High productivity reaction volume;

Elimination of reactor agitator and agitator seals;

Efficient Catalyst Systems;

Low or no off-gas waste-stream rate;

Employment of an ultra-high ratio of gas/liquid interfacial area to liquid reaction volume;

Employment of an ultra-low ratio of liquid reaction volume to liquid volume contained in the liquid-film diffusion zone attached to the gas interface;

Variation and accurate control of the ratio of gas/liquid interfacial area to liquid reaction volume, and the ratio of liquid reaction volume to liquid volume contained in the liquid-film diffusion zone attached to the gas interface;

Multi-parameter control of liquid reactant conversion;

Multi-parameter control of liquid reaction mass temperature;

Avoidance of solids buildup in the reactor;

Internal condensation; and

Easy recovery of high purity, high oxygen-concentration off-gas for recycle with low recompression requirements.

This invention provides a more productive reaction volume than does the conventional technology. Reaction chamber productivity per unit liquid reaction volume is increased due to the greatly enhanced mass transfer rates afforded by this invention, coupled, if so desired, with measures to maximize droplet loading in the reaction chamber. Droplet loading in the reaction chamber may be maximized according to the present invention, by employing internal condensation and generating ultra-small liquid reaction droplets. The droplet loading, measured as a percent of reaction chamber volume occupied by the totality of the droplets in the reaction chamber at any one time, is preferably maintained in the range of 1–40%. More preferably, droplet loading is maintained in the range of 5–30%. More preferably still, droplet loading is maintained in the range of 10–20%. Excessively high droplet loading can lead to sudden and uncontrolled coalescence, and is to be avoided. Too low droplet loading can lead to low reaction chamber productivity. The optimal control of droplet loading and initial droplet size minimizes the coalescence of droplets, while in the reaction chamber, optimizes the mass transfer of oxygen or other oxidant from the gas phase to the liquid phase, and maximizes the liquid reaction volume available to support the desired product formation.

As it will become clear in the course of this discussion, unlike in the conventional technology which utilizes sparging of oxidizing gases through mechanically agitated liquids containing reactants to be oxidized, there is no reaction chamber agitator and no agitator seals. This process simplification is made possible by the unique reaction environment provided by this invention, and is highly desirable as it reduces cost, investment, and improves plant utility compared to the conventional technology.

Since according to the present invention the reaction is conducted within the droplets, which are in a liquid phase, the process still maintains the advantage of being able to employ efficient liquid-soluble catalyst systems, with the added advantage of attaining reaction conditions almost as efficient as those encountered in a homogeneous gaseous phase. Reactions in a gaseous phase would require costly and uncertain gas-phase catalysts or solid-phase catalyst systems.

Further, this invention enables a low off-gas waste-stream rate, if so desired, which reduces the off-gas waste-stream rate to the environment, and reduces off-gas cleanup investment and costs, thus resulting in considerable environmental improvement. The low off-gas waste-stream rate may be made possible with a near-stoichiometric gaseous oxygen feed combined with high conversion rates and/or chemical yields, for example.

In the conventional technology, reaction chamber non-condensible off-gas is commonly purged to the atmosphere without partial recycle back to the reaction chamber. This results in increased oxygen consumption and related cost, but is done to avoid high, non-economic recompression costs and investment. In the conventional technology, recompression costs and investment are high due to a high non-condensible load, and high recycle pressure requirement:

high non-condensible load results from the relatively high chemical yield loss, and—in most instances—the use of air as the oxygen source;

high recycle pressure is required to accommodate the high-pressure drop, subsurface sparging (into a liquid-filled reaction chamber) used in the conventional technology;

the high-pressure drop is required, in the case of subsurface sparging, to overcome the liquid head in the reaction chamber and to provide high-power mixing; and high-power mixing is necessary, in the case of the conventional technology, to improve gas/liquid contacting and thereby accelerate the rate of oxygen transfer into the liquid phase.

When condensation is employed at a stage before the pressure drop (internal condensation), the increased oxygen consumption and related cost, and the high, non-economic recompression costs and investment associated with the conventional technology are avoided. Internal condensation according to this invention is condensation of condensibles, which takes place within the pressurized system and before pressure drop to about atmospheric pressure. Inside condensation or inside internal condensation is condensation which takes place within the reaction chamber. According to this embodiment, it is possible to recycle oxygen-containing off-gas back to the reaction chamber with relatively low or no recompression requirement and cost. The recycle may be even eliminated without incurring significant adverse economic impact. When condensation is employed at such a stage, the recompression requirement is minimal—compared to the conventional technology—due to the low non-condensible off-gas rate, especially when near-stoichiometric oxygen feed is used. The low non-condensible off-gas rate is due to the combination of near-stoichiometric oxygen feed, with one or more of high second reactant conversion rate, high chemical yield, and internal condensation, enabled and provided for by the instant invention.

According to the instant invention, when near-stoichiometric oxygen feed is desired, it is achievable by the high conversion of the oxygen feed to the reaction chamber per pass, hence needing little recycle requirement. The high chemical yield results in low non-condensible by-product formation, thereby significantly reducing off-gas purge load generated in the reaction chamber. Reduced off-gas purge load in turn reduces oxygen purge from the reaction chamber. Reduced oxygen purge from the reaction chamber minimizes oxygen recycle requirement. The implementation of internal condensation further reduces recompression requirement, as internal condensation outside the reactor further reduces oxygen recycle required, and the implementation of internal condensation inside the reactor reduces oxygen recycle requirement further still. This internal condensation significantly reduces oxygen physical yield-loss. In the limit, internal condensation, complete oxygen conversion per pass, i.e., stoichiometric oxygen feed, and zero non-condensible by-product formation would result in zero oxygen physical yield loss and zero recompression requirement. Due to the low non-condensible off-gas rate made possible when internal condensation is employed, it is significantly less costly (compared to the conventional technology) to forego recycle.

In this invention, solids buildup in the reaction chamber may be prevented by washing the walls of the reaction chamber with preferably cooler, preferably catalyst-free liquid solvent, or with preferably catalyst-free liquid reactant, or with a mixture thereof. All surfaces of the reaction chamber, or a certain portion of those surfaces prone to solids buildup, may be washed in this manner. The wash liquid may be sprayed onto the surfaces so washed, or may be generated in situ as a result of internal condensation. Solids buildup is prevented because the solids in contact with these surfaces are continuously washed out of the reaction chamber. Furthermore, reaction in the wash-liquid is greatly minimized by the lower temperature or absence of catalyst, the short hold-up-time or a combination thereof. All solids produced in the reaction chamber are removed from the reaction chamber with the wash liquid.

In the embodiments of this invention involving off-gas recycle, this invention provides means by which the recompression requirement can be greatly minimized or eliminated. Due to the small non-condensible off-gas rate associated with this invention, it is possible to educt the recycle off-gas into the reaction chamber using a liquid stream as the motive force.

In the conventional technology, gas sparging bubbles are dispersed in a continuous liquid-phase comprised of liquid reactants, liquid solvents, dissolved reaction products and by-products, dissolved gases, and dissolved catalysts. A thin film of liquid is attached and surrounds each bubble, due to strong surface tension forces. While the thickness of the liquid-film is a function of many variables including, but not limited to, temperature and viscosity of the liquid solvent and liquid reactant, generally the thickness of the liquid-film is in the range of 0.05 inches to 0.0001 inches, and mostly in the range of 0.02 inches to 0.001 inches. Reactions can occur in this liquid-film and in the continuous-phase liquid surrounding this film. Reaction products may in fact be preferentially produced in the film, relative to the surrounding liquid, depending on the nature of the diffusional resistance inhibiting the transfer of materials from the liquid film into the surrounding liquid. In any event, it is expected that a significant amount of reaction will occur in the liquid-film due to its immediate proximity to the gas-phase second reactant, such as oxygen or other oxidant for example. In the conventional technology, the ratio of liquid reaction volume to liquid volume in the liquid-film is extremely high—typically, this would be several orders of magnitude. This extremely high ratio leads to two highly undesirable consequences:

First, it leads to gross non-homogeneities in the concentration of reaction products between the two zones, with high localized product concentrations building up in the liquid-film. These high localized concentrations arise in the liquid-film in the conventional technology because a significant (perhaps even predominant) amount of reaction occurs in the liquid-film due to its immediate proximity to the gas-phase reactant, and because reaction products so formed in the liquid-film must necessarily increase in concentration—relative to the surrounding bulk liquid—to overcome diffusional resistance and migrate from the liquid-film out into the surrounding liquid. Furthermore, for a given production rate and conversion, the higher the ratio the higher the product concentration in the liquid-film. The worst consequence of high localized product concentration in the liquid-film in the conventional technology is that it leads directly to over-reaction products, such as over-oxidation for example. Over-oxidation results when already formed product continues to be exposed to reactive forms of oxygen. Over-oxidation in turn causes chemical yield loss, high product purification costs, and high waste disposal costs.

Second, it leads to poor utilization of the total available reaction volume. This results because the most productive reaction volume is that in closest proximity to the gas-phase oxygen. The reaction volume closest to the gas-phase oxygen is the liquid-film. At very high ratios the amount of volume occupied by the liquid-film is extremely small; hence, the poor utilization at high reaction volume.

This invention overcomes the aforementioned problems associated with the conventional technology by converting the reaction system to ultra-low ratio of liquid reaction volume to liquid volume in the liquid-film. This is the exact opposite of the conventional technology. In this invention, ultra-low ratios are obtained by converting the bulk stirred liquid phase to spray droplets of controlled small size suspended in the continuous gas-phase. The size of the droplets may be controlled such that the average radius of the droplet is preferably less than about 10 times the thickness of the diffusion film associated with the conventional technology. More preferably, the droplets should be controlled such that the average radius of the droplet is on less than about 5 times the thickness of the diffusion film associated with the conventional technology. More preferably still, the droplets are to be controlled such that the average radius of the droplet is less than about 1 time the thickness of the diffusion film associated with the conventional technology. In this way, the ratio can be decreased by orders of magnitude below that possible in the conventional technology. This is highly desirable because it enables a significant reduction in over-reaction with concomitant reduction in impurity levels, reduction in purification costs and investment, and reduction in waste-stream load, without loss of production rate, and with more efficient utilization of liquid reaction volume in the reaction chamber (compared to the conventional technology).

Further, in the conventional technology, the ability to generate a high ratio of gas/liquid interfacial area to liquid reaction volume is constrained by natural effects (including liquid surface tension) to certain practical maximums. Heroic efforts, including high gas sparging rates and powerful agitation systems, have been employed to achieve operation near the upper maximum limit. The inventors theorized that a much higher ratio would be desirable, since it would facilitate the diffusion of oxygen reactant into a liquid film surrounding each gas bubble. This film is strongly attached to the bubble by strong surface tension forces. Reaction can occur in this film and in the continuous-phase liquid surrounding this film, and the ability to effect reaction in either zone is dependent on oxygen diffusion from the gas-phase into the film. In the conventional technology, higher diffusion rates may be only achieved by either increasing oxygen or other oxidant concentration in the gas passing through the liquid reaction phase, or by increasing the gas sparging rate. However, this is of very limited value, and only small improvements in diffusion rates may be made.

In contrast, according to this invention, huge improvements in diffusion rates may be made by using ultra-high ratios of gas/liquid interfacial area to liquid reaction volume, which are obtained by converting the bulk stirred liquid phase into spray droplets of controlled small size within a continuous gas-phase. For this purpose also, the size of the droplets should be controlled such that the radius of the droplet is on average preferably less than about 10 times the thickness of the diffusion film associated with the conventional technology. More preferably, the droplets should be controlled such that the radius of the droplet is on average less than about 5 times the thickness of the diffusion film associated with the conventional technology. More preferably still, the droplets are to be controlled such that the radius of the droplet is on average less than 1 time the thickness of the diffusion film. By this method, the ratio of gas/liquid interfacial area to liquid reaction volume can be increased by orders of magnitude above that possible in the conventional technology. This is highly desirable because it enables a significant reduction in the oxygen concentration in the gas-phase without loss of production rate (compared to the conventional technology), or, alternately, higher oxygen diffusion rates (hence higher production rates) at comparable oxygen concentration in the gas-phase.

The significant reduction in the oxygen concentration in the gas-phase, concurrent with still maintaining desirable high reaction rates, made possible by this invention, is extremely desirable because it acts to improve yield by reducing over-oxidation, improve safety by enabling operation further away from the oxygen/fuel explosive envelope, and minimize the amount of oxygen swept from the reaction chamber. Minimizing the amount of oxygen swept from the reaction chamber with other non-condensibles is desirable because it significantly reduces: (1) costly investment for waste off-gas environmental cleanup facilities, (2) waste off-gas discharges to the environment, thus providing considerable environmental improvement, and (3) very expensive, high maintenance, and potentially unsafe recompression requirements (all three of which cause problems in the conventional technology).

According to the present invention, variation and accurate control of the ratio of gas/liquid interfacial area to liquid reaction volume, and the ratio of liquid reaction volume to liquid volume contained in the liquid-film at the gas interface are provided. Since, in the present invention, the gas-phase is the continuous-phase, both ratios may be simultaneously controlled by controlling the average droplet size and the droplet size distribution spectrum. For small droplets, surface tension forces will pull the droplets into near spheres. For spherical droplets, the ratio of gas/liquid interfacial area to liquid reaction volume is inversely proportional to droplet diameter, and the ratio of liquid reaction volume to liquid volume contained in the liquid-film is directly proportional to droplet diameter. Consequently, ultra-high ratio of gas/liquid interfacial area to liquid reaction volume and ultra-low ratio of liquid reaction volume to liquid volume contained in the liquid-film can be simultaneously achieved and controlled by reducing droplet diameter to very small, controlled diameters. Specifically, as aforementioned, the size of the droplets is to be controlled such that the diameter of the droplet is on average less than 10 times the thickness of the liquid-film associated with the conventional technology. However, since droplets of increasingly small size contain dimimous reaction volume, and since little further advantage is to be gained in enhanced reaction rate and reduced over-reaction, preferably the droplets are to be controlled such that the diameter of the droplet is more than 0.5 times the thickness of the liquid-film associated with the conventional technology. More preferably the droplets are to be controlled such that the diameter of the droplet is more than 1 time the thickness of the liquid-film associated with the conventional technology. While the thickness of the liquid-film associated with the conventional technology is a function of many variables including, but not limited to, temperature and viscosity of the liquid solvent and liquid reactant, generally the thickness of the liquid-film is in the range of 0.05 inches to 0.0001 inch. In absolute terms the preferred average droplet diameter is in the range of 0.001 to 0.2 inch.

The ways to control average droplet diameters in atomization is well-known to the art, and it includes, but is not limited to, nozzle design, variable nozzle characteristics, pressure of atomized material, pressure of gas if gas is used for the atomization process, and the like.

The control of conversion within tight ranges and at desired levels is critical to a well run process. Erratic control leads to poor chemical and physical yields, process upsets, high purification costs, high trace impurity levels, high recycle requirements, lost utility, and reduced plant capacity. Too low conversion results in high recycle requirements, reduced physical yield, higher unit plant investment, higher unit energy consumption, and reduced plant capacity. Too high conversion leads to over-reaction, poor chemical yields, high purification costs, high trace impurity levels, higher unit plant investment, and reduced plant capacity. In this invention, multiple ways are provided to control conversion. Conversion may be controlled at a desired level by manipulation of variables, either alone or in combination with each other. Some of these variables are:

Oxygen concentration in the reaction chamber.

The ratio of the concentrations of liquid solvent to liquid reactant in the liquid feed to the reaction chamber.

The concentration of catalyst in the liquid feed to the reaction chamber.

The hold-up time of the liquid feed in the reaction chamber.

The size or diameter of the droplets in the reaction chamber.

The temperature of the droplets.

According to this invention, conversion can be controlled, for example, by regulating the oxygen concentration in the reaction chamber. This is to be done by using oxygen as the limiting reagent. In this instance, the rate of oxygen feed to the reaction chamber would be increased or decreased as required to control conversion. Conversion is increased—holding all other parameters constant—by increasing oxygen feed rate, and thereby increasing oxygen concentration in the reaction chamber. Conversion is decreased—holding all other parameters constant—by decreasing oxygen feed rate, and thereby decreasing oxygen concentration in the reaction chamber.

Further, conversion is increased—holding all other parameters constant—by increasing the concentration of catalyst in the liquid feed to the reaction chamber. Conversion is decreased—holding all other parameters constant—by decreasing the concentration of catalyst in the liquid feed to the reaction chamber.

In addition, conversion is increased—holding all other parameters constant—by increasing the hold-up time of the liquid feed in the reaction chamber. Conversion is decreased—holding all other parameters constant—by decreasing the hold-up time of the liquid feed in the reaction chamber. Hold-up time of the liquid feed in the reaction chamber is controlled by varying the height of the gas-phase through the droplets fall. Hold-up time is increased by increasing the height, and decreased by decreasing the height. The height may be controlled in several ways. For example, it may be controlled by:

Raising or lowering the height of the droplet spray nozzle or nozzles.

Raising or lowering the height of a liquid pool at the liquid level at the end of the vertical reaction chamber. The height of the liquid pool can be determined and controlled by a variety of ways well known to the art.

Also, conversion is increased—holding all other parameters constant—by decreasing the size of the liquid droplets in the reaction chamber. Conversion is decreased—holding all other parameters constant—by increasing the size of the liquid droplets in the reaction chamber. Droplet size inversely affects conversion by controlling oxygen mass transfer into the liquid reaction media. Since the ratio of surface area to volume for a spherical droplet is inversely proportional to the diameter of a droplet, and since oxygen transport from the gas-phase is directly proportional to the surface area of a droplet, then the ratio of oxygen mass transport to the liquid volume contained in a droplet varies inversely with the diameter of the droplet. Therefore, the relative oxygen mass transfer for larger droplets is smaller than that for smaller droplets, and conversion is correspondingly reduced when all other parameters are held constant.

Because reaction rates are faster at higher temperatures, in this invention, conversion is increased—holding all other parameters constant—by increasing the temperature of the liquid droplets. Conversion is decreased—holding all other parameters constant—by decreasing the temperature of the liquid droplets in the reaction chamber.

According to this invention, the heat of reaction may be removed from the liquid reaction mass as vaporized liquid reactant and vaporized liquid solvent. These vaporized materials may be condensed either outside or inside the reaction chamber as it will be discussed hereinbelow. Removal of heat inside the reaction chamber may be conducted for example by using condensation sprays, or condensation surfaces, or a combination thereof.

It should be stressed that internal condensation may take place either outside or inside the reaction chamber, as illustrated later. Internal condensation is condensation which takes place within the system, before the pressure is relieved. Internal or external (outside the pressurized system) should not be confused with inside (inside the reaction chamber) and outside (outside the reaction chamber) conversion.

In the case of condensation sprays, a portion of recycled liquid may be cooled in a heat exchanger or brought to a desired temperature by other temperature control means well known to the art, external to the reaction chamber, and be sprayed onto the interior reaction chamber walls, or into the gas-phase of the reaction chamber, or both. In the case where said spray is directed onto the reaction chamber wall, and in the instance where reaction products are relatively insoluble in said spray, then streams after filtering out the reaction products are preferable. The absence of catalyst in this case is also important, because this absence and the relatively cold nature of the incoming streams act to prevent reaction in said spray on the interior wall of the reaction chamber. In the case where reaction products are relatively insoluble, this absence of reaction prevents the highly undesirable accumulation of solids on this surface. Condensation spray is effective because hot, condensible gases inside the reaction chamber condense on the cool, liquid surface. The amount of condensation induced in this manner may be controlled by regulating the flow rate, temperature, and position of the condensation spray. Increasing the flow rate, decreasing the temperature, and controlling the condensation spray so as to increase its liquid surface area act individually or in combination to increase the rate of condensation of the vaporized liquid containing the reactant and vaporized liquid solvent; the converse is also true.

Furthermore, in the case of condensation sprays, this invention provides both the means to control the liquid surface area of the condensation spray, and the means to prevent excessive contact of the reaction liquid spray with the condensation spray. Where condensation spray is directed against the side of the reaction chamber wall, the condensation surface area may be effectively controlled by manipulating the impingement position of the condensation spray nozzles on the side of the reaction chamber wall. Directing this spray higher up the side of the reaction chamber wall increases the condensation surface area. Conversely, directing it lower decreases the condensation area. Where the condensation spray is directed into the gas-phase of the reaction chamber, the condensation surface area may be effectively controlled by manipulating the size and amount of the droplets. Since the ratio of surface area to volume for a spherical droplet is inversely proportional to the diameter of a droplet, and since the cumulative volume of all of the droplets sprayed into the reaction chamber is fixed for a given flow rate, then the surface area may be easily and precisely increased—when all other parameters are held constant—by decreasing the droplet size. The converse is also true. Droplet size can be easily controlled using techniques well known to the art.

Furthermore, in the case of condensation sprays, it is critical to prevent excessive contact of the reaction liquid spray with the condensation spray. This is true because the condensation spray may not contain catalyst and is deliberately cooled well below the reaction temperature of the liquid reaction media. Excessive mixing of these two sprays could result in a significant reduction in condensation efficiency, reaction rate, or both. Excessive mixing may be prevented in the first instance by positioning the spray nozzles so as to direct the condensation spray against the reaction chamber wall, and the liquid reaction spray into the gas-phase of the reaction chamber in a manner which minimizes wall contact. In the second instance, excessive mixing may be prevented by selecting a spray nozzle for the condensation spray which produces a very small diameter droplet. This technique is effective because very small droplets do not readily mix with similar, smaller, or larger sized droplets, thereby preventing the undesired contact with the liquid reaction spray. Furthermore, producing a very small condensation spray droplet is highly efficient, from the standpoint of the desired condensation of vaporized liquid reactant and vaporized liquid solvent, because it increases the condensation surface area.

In the case of condensation sprays, and in the second instance, where the condensation spray is directed into the gas phase of the reaction chamber and where excessive mixing is prevented by selecting a spray nozzle for the condensation spray which produces a very small diameter droplet, this invention provides a reaction system in which the liquid contents of the reaction chamber are comprised of two different droplet types: both types simultaneously occupy the same reaction environment and each is in close proximity to the other, but each type remains separate, each may contain different concentrations of liquid solvent and liquid reaction chemicals, each type may be at significantly different temperatures, and each may perform different functions (namely, either condensation or reaction).

In the case where vaporized liquid reactant and vaporized liquid are condensed inside the reaction chamber on metal surfaces, this may be accomplished in the first instance by externally cooling the reaction chamber walls with an external cooling jacket through which is circulated a cooling medium, like cooling water; or, in the second instance, by providing a cooling coil or other cooling surface inside the reaction chamber through which is circulated a cooling medium, like cooling water. In the first instance, condensation occurs inside the reaction chamber when condensible gases come into contact with the externally cooled reaction chamber walls. The walls cooled by this method may be the vertical sides of the reaction chamber, or the top, or the bottom, or a combination thereof. In the second instance, condensation occurs when the condensible gases come into contact with the internal cooling coils or other cooling surfaces inside the reaction chamber.

According to this invention, non-condensible gases are swept away from the condensation surfaces (regardless of whether these condensation surfaces are the ones produced by the use of condensation sprays or by solid surfaces) by gaseous eddie currents inside the reaction chamber. These eddie currents may be induced by the combined liquid sprays inside the reaction chamber. The efficient removal of the non-condensible gases from the condensation surfaces is critical, because unless this is done, the condensation surfaces become blanketed by the non-condensibles, and the desired condensation is greatly diminished.

As already discussed, according to this invention, non-condensible reaction by-product gases may be purged from the reaction chamber through an overhead gas outlet or they may be purged out the bottom of the reaction chamber. In the former case, the small diameter liquid reaction droplets, or the small diameter liquid reaction droplets along with very small condensation spray droplets, produced according to the methods of this invention, fall to the bottom of the reaction chamber, where they coalesce and exit the reaction chamber. In the latter case, the small diameter liquid reaction droplets, or the small diameter liquid reaction droplets along with the very small condensation spray droplets, either fall to the bottom of the reaction chamber and coalesce there, or are swept by the non-condensible purge gases into a swirling vortex at the bottom of the reaction chamber and, thereby, are brought into extremely close proximity with the liquid, where they coalesce, as it will be discussed in more detail later. The extremely close contact so induced is sufficient to coalesce the small diameter liquid reaction droplets, or the small diameter liquid reaction droplets along with the very small condensation droplets, from the gas purge into the liquid phase. In both cases, therefore, the liquids exiting the bottom of the reaction chamber may remove both the reaction liquid spray, and the condensation spray, if present, from the reaction chamber.

Control of droplet impingement (to each other) resulting in increase of droplet size is very important, and as mentioned above, it may be controlled by controlling the droplet size of the first liquid or the second liquid or both. Reduction of the droplet size and decrease of the reactor loading favor the avoidance of impingement. Loading of the reactor is defined as the total volume of liquid divided by the total volume of the reactor.

Monitoring carbon monoxide and carbon dioxide in the off-gases is a prudent precaution, since unexpected or higher than normal amounts of carbon monoxide and/or carbon dioxide signify poorly controlled or uncontrolled oxidation. Similar overriding rules applied by the controller help in preventing poor yields, conversions, and even explosions.

In addition, carbon monoxide is harmful to the atmosphere and the reaction should be driven in a way to avoid its formation as much as possible. Optimization of the reaction conditions according to the instant invention has a beneficial effect in this respect.

Our patent applications Ser. No. 08/477,234, U.S. Pat. No. 5,502,245 Ser. No. 08/478,257, U.S. Pat. No. 5,580,531 Ser. No. 08/477,195, and Ser. No. 08/475,340, U.S. Pat. No. 5,558,842 all of which were filed on Jun. 7, 1995, and all of which are incorporated herein by reference, disclose and claim miscellaneous methods and apparatuses for controlling reactions in general with special emphasis to oxidations, which may be combined with the embodiments of the present invention in any suitable manner, thus increasing even further waste minimization and resulting in considerable environmental improvement.

Referring now to FIG. 1, there is depicted a conventional reactor 10, comprising a reaction chamber 11, connected to a condenser 12, which in turn is connected to a valve 13. A gas line 14 is also provided close to the bottom of the reaction chamber 11 for bubbling gas through a liquid containing a reactant, which reactant reacts with the gas a component of the gas to form a reaction product. The reaction chamber 11 may be pressurized, especially when the temperature required for the reaction to take place is higher than the boiling point of the liquid. This situation is very often encountered in the case of reactions involving organic compounds. Examples include, but are not limited to formation of cyclohexanone or cyclohexanol, or cyclohexylhydroperoxide, or adipic acid from cyclohexane by oxidation of the latter, usually by oxygen. Similar examples include formation of phthalic, isophthalic, or terephthalic acid by oxidation of the corresponding xylenes.

This type of condensation may be labeled as internal outside condensation, since it takes place within the pressurized zone (internal), but outside the reaction chamber (outside).

In this conventional case, large amounts of gases have to pass through the liquid in the form of gas in order to achieve an appreciable degree of reaction. This may not be true in the case of salt formation, where for example, an acidic gas passes through an alkaline liquid. However it is true for most organic reactions of this sort, and especially controlled oxidations (leading to intermediate oxidation products, other than carbon monoxide and/or carbon dioxide), wherein special attention has to be paid for avoiding combustion, or even explosion. The amount of gases increases even further if the gaseous reactant, such as oxygen for example, is diluted with an inert gas, such as nitrogen for example. In order to keep the gaseous flow adequately high for the reaction, and maintain the pressure within acceptable limits, valve 13 has to be open enough to allow the voluminous unreacted gases to escape to the environment. Recirculation of the high volumes of gases into the system is difficult and uneconomical.

The main purpose of the condenser 12 in this conventional case of FIG. 1, is to remove condensibles from the voluminous gases before they escape to the environment. However, no matter how efficient the condenser 12 is, a small amount of condensibles will escape through valve 13 along with the gases. In reactors, such as the one illustrated in FIG. 1, removal of heat could be accomplished by direct cooling of the liquid, since the temperature of the liquid is actually the temperature which has to be controlled. Direct cooling of the liquid may be done, for example, with a jacket around the liquid or by a coil within the liquid. The gas/liquid interface, however, is too small in most cases for efficient cooling. In most cases the heat is removed by a volatile solvent in the liquid which evaporates during the course of the reaction. In the case of highly exothermic reactions, the massive amounts of evaporated solvent force large amounts of the gaseous reactant, such as oxygen for example, to follow the same path and finally be removed through valve 13. Recirculation of the gaseous reactant is very expensive, since it requires efficient high pressure compressors.

In the reactor of FIG. 1, even if one had the valve 13 substantially closed, and were feeding just enough gaseous reactant, such as oxygen for example, to maintain a desired pressure by replacing the reacted amount of gaseous reactant with the liquid, comprising cyclohexane for example, the condenser would be filled with non-condensible gases at an early point, and condensation of condensibles would be reduced drastically if not ceased altogether.

An internal (within the pressurized system) inside (within the reaction chamber) condenser (not shown) would not serve much of a purpose, since the liquid/gas interface is too small, and removal of reaction heat by condensation as a primary means heat removal would not be practical in this conventional arrangement.

Figure 2:
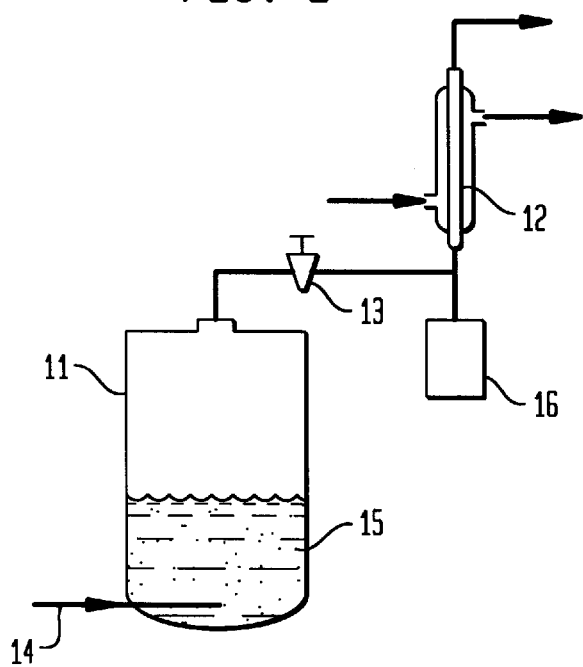
FIG. 2 illustrates schematically another conventional reactor using external condensation.

Another conventional arrangement is illustrated in FIG. 2, wherein the condenser 12 is located after the valve 13, and outside the pressurized zone. In this case an additional condensate tank 16 to collect the condensed condensibles, which may be recycled into the system. The problems described in the previous case become even more acute in this arrangement, especially with respect to increased contamination of the off-gases.

Figure 4:
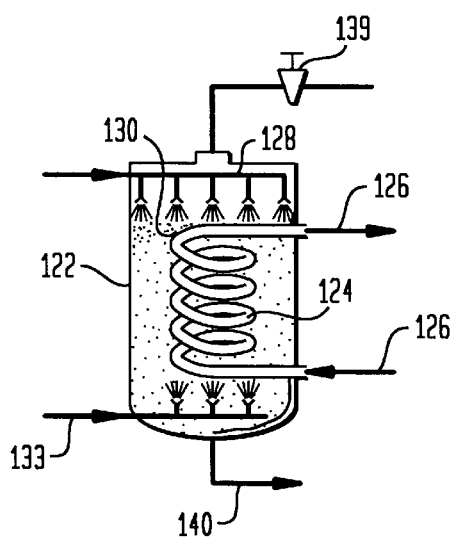
FIG. 4 illustrates schematically still another preferred embodiment of the present invention, wherein a first liquid is atomized and condensation takes place on a solid surface cooled by a coil within the reaction chamber.
Figure 5:
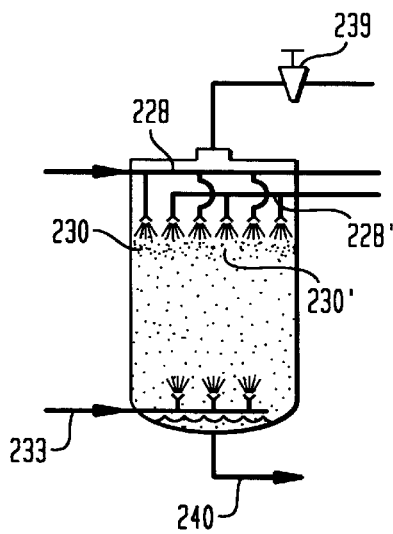
FIG. 5 illustrates schematically a highly preferred embodiment of the present invention, wherein a first liquid is atomized and condensation takes place on a liquid surface comprised of droplets of a second liquid having a lower temperature than the first liquid and being co-atomized with the first liquid.

In contrast to the above conventional systems, internal inside condensation may be used very efficiently according to the present invention. Three exemplary arrangements are shown in FIGS. 3, 4, and 5.

Figure 3:
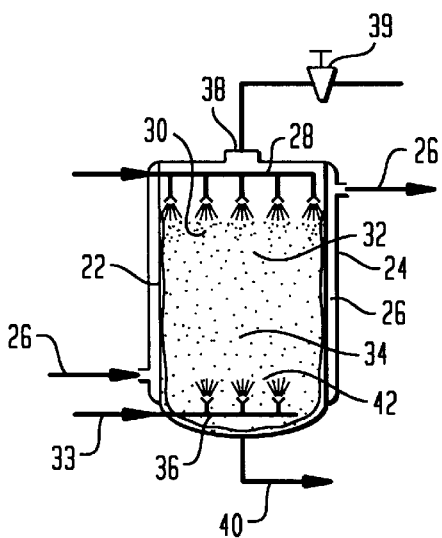
FIG. 3 illustrates schematically a preferred embodiment of the present invention, wherein a first liquid is atomized and condensation takes place on a solid surface cooled by a jacket around the reaction chamber.

In one embodiment of this invention, the reactor comprises a reaction chamber 22 as better illustrated in FIG. 3. The walls of reactor 22 are surrounded by a condenser in the form of a jacket 24. In the case that condensation is desired, a liquid 26, having a suitably low temperature, may be circulated in the jacket 24. The jacket 24 may also be used to heat-up the walls of the reaction chamber 22, by steam for example, if so desired.

A first atomizer 28 having a plurality of nozzles 30 is disposed within the reactor, preferably at the upper end 32.

The reaction chamber 22 is also provided with a gas line adapted to distribute a gas within the reaction zone 34 through a plurality of orifices 36. A gas exit port 38 is preferably located at the vicinity of the upper end 32 of the reaction chamber 22, and it is connected to valve 39. Further, a liquid exit port is preferably located in the vicinity of the lower end 42 of the reaction chamber 22.

The reaction chamber 22 is preferably adapted to withstand such temperatures and pressures, which are appropriate for the reaction conditions in the reaction chamber 22, and be suitable for the reactants and reaction products. Such materials and construction characteristics are well known to the art. For example, depending on the particular reaction, carbon steel, stainless steel, or Hastalloy may be required. In addition, the inside surface may be protected by coatings or linings of vitreous or other materials, such as glass or titanium, respectively for example.

The atomizer 28 is preferably of the airless type (does not need an atomizing gas for its operation). Airless atomizers are well known to the art. The atomizer 28 may be steady at a certain position of the reaction chamber 22, or it may be movable, preferably in an up/down mode.

Figure 6:
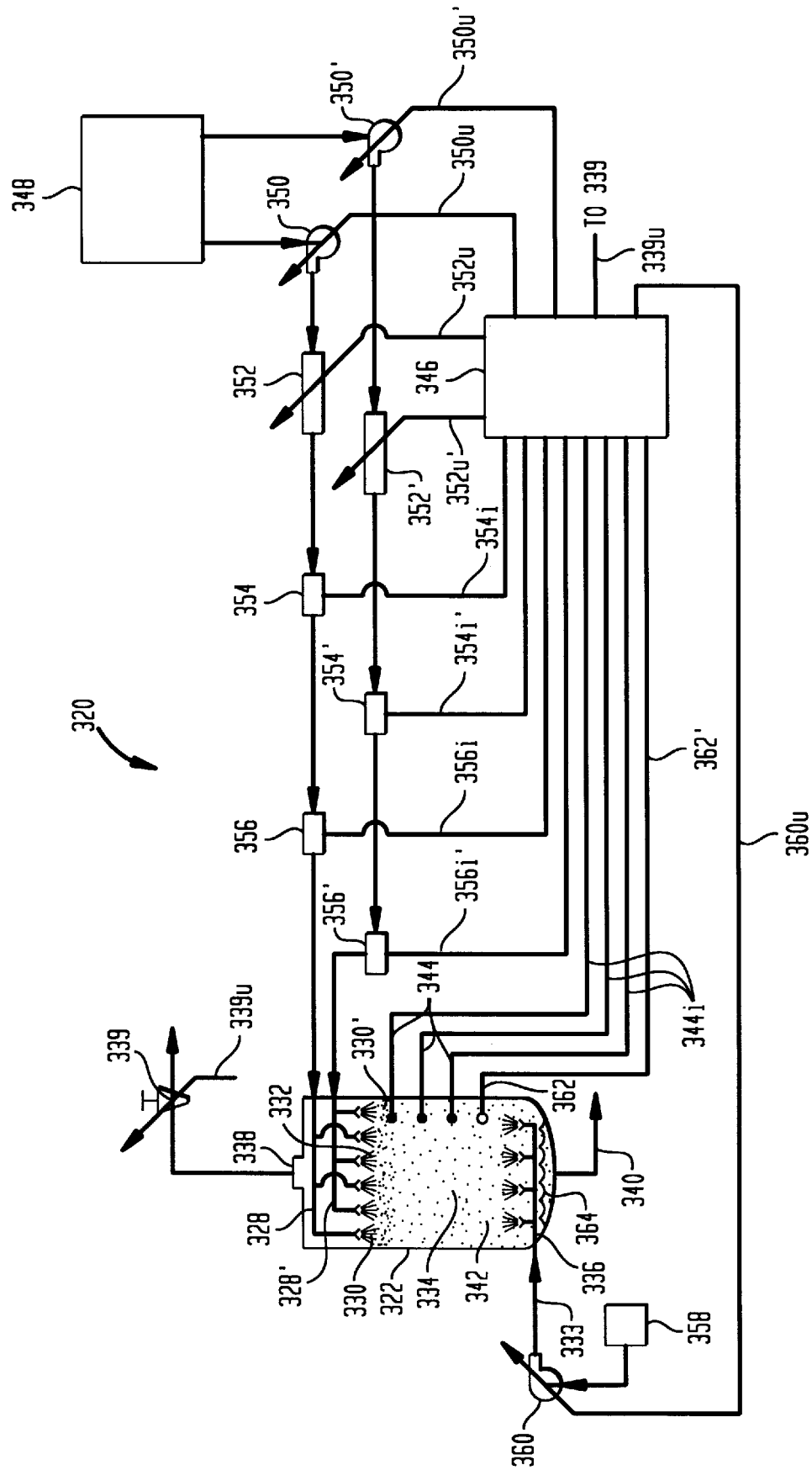
FIG. 6 illustrates schematically an exemplary control arrangement, which may be utilized along with the miscellaneous embodiments of the instant invention.

In operation of this embodiment, a first liquid, for example a mixture of cyclohexane, a solvent such as acetic acid for example, a catalyst, such as a cobalt salt for example, an initiator, such as cyclohexanone or acetaldehyde for example, and other desirable adjuncts, in proportions which may be similar to the ones described in the art for conventional systems, and at an atomization temperature, enters the reaction chamber through the first atomizer 28 and nozzles 30 in the form of atomized or sprayed first droplets. The first liquid comprises a first reactant, which is cyclohexane in this example. At the same time that this atomization is taking place, a gas containing a second reactant, such as oxygen for example enters the system though gas line 33 and the plurality of orifices 36 and moves in a substantially opposite direction than the first droplets. As the first droplets proceed within the reaction zone 34 from the upper part 32 toward the lower part 42 of the reaction chamber 22, the second reactant, oxygen for example, reacts at least partially with the first reactant, cyclohexane for example. During the reaction, heat is generated, which raises the temperature of the first droplets. As the temperature of the first droplet rises, evaporation of first liquid or components thereof takes place, thus lowering the temperature of the droplets. Droplet temperature may be controlled by controlling the rate of evaporation. Control of the rate of evaporation may be conducted by maintaining constant reactor pressure and by adjusting the rate of condensation of vapors on the condensing walls of the reaction chamber. This in turn is achieved by adjusting the temperature and rate of heat absorbed by the condenser in the form of jacket 24. Details of how is this carried out are discussed in a later section with reference to FIG. 6. Although FIG. 6 illustrates this for the embodiment of FIG. 5, all condensing mechanisms of this invention may be substantially controlled in the manner described with reference to FIG. 6.

In contrast to the reaction chambers illustrated in FIGS. 1 and 2, the liquid/gas interface is huge in the case of the reaction chambers of this invention, and thus, condensation can be an excellent controlling factor of the rate of evaporation from the first droplets, and in turn an excellent control of the temperature of the first droplets.

The excess gas is removed through gas exit port 38 and valve 39, while the first liquid is removed through liquid exit port 40.

The pressure within the reaction chamber is controlled by the flow rate at which the gas enters the reaction chamber 22 through orifices 36 and the degree of opening of the valve 39, as well as the liquid condensate temperature.

If the reaction is not complete by the time the first droplets reach the lower end of the reaction chamber, the first liquid may be partly or totally recirculated from the liquid exit port to the first atomizer 28, as is or after some treatment, well known to the art, to remove partially or substantially totally the reaction product and/or other adjuncts.

A tremendous difference between the reactors of this invention (illustrated in FIG. 3 for example) and the conventional reactors (illustrated in FIG. 1, for example) is that in the former case recirculation of liquids, which is very easy, may be required, while in the latter case, recirculation of gases may be necessary.

Thus, in the case of this invention, the valve 39 may be substantially closed, and second reactant be introduced to the reaction chamber 22 per reaction needs, while merely recirculating the first liquid from the liquid exit port 40 back to the first atomizer 28. In contrast, if the same is desired for the conventional reactor illustrated in FIG. 1, the gas will have to be recirculated, which is a rather undesirable task.

An additional advantage of the instant invention is that the temperature of the first droplets, which represent a rather small mass, may be controlled quickly and easily by internal inside condensation. In contrast, the big mass of liquid involved in conventional technology is necessarily very slow regarding forced temperature changes.

In another embodiment of this invention, better illustrated in FIG. 4, a condensation coil 124 is used in lieu of the jacket 25 of FIG. 3. The operation of this embodiment regarding internal inside condensation is substantially the same as described hereinabove for the embodiment of FIG. 3, with the difference that the internal inside condensation takes place on the coil 124 instead of the walls of the reaction chamber 122.

In still another highly preferred embodiment of the instant invention, better illustrated in FIG. 5, there is provided a second atomizer 228' in addition to the first atomizer 228. The second atomizer 228' is adapted to form second droplets through nozzles 230' from a second liquid. The second droplets have a lower temperature than the first droplets formed by atomizer 228, and they are used as condensing means of vapors produced by evaporation of components from the first droplets.

Although the second droplets produced from the second liquid may have any desired composition, it is preferable that they have at least one ingredient in common with the first droplets produced from the first liquid. It is more preferable that, if the first droplets comprise a first set of ingredients and the second droplets comprise a second set of ingredients, the first and second sets comprise the same ingredients. It is even more preferable that the two sets comprise the same ingredients under the same proportions. As a matter of fact, the first and the second droplets may be parts of the first liquid, which first liquid has been divided into two streams, a first stream corresponding to the first droplets, and the second stream corresponding to the second droplets. The basic difference between the first and the second droplets is that they are introduced to the reaction chamber at different temperatures (higher temperature for the first droplets, and lower temperature for the second droplets), and maybe different flow rates. The first droplets are utilized to perform the reaction, while the second droplets have as a main function to condense vapors produced by the first droplets, as the reaction proceeds and the temperature of the first droplets increases. Mixing of the two types of droplets with each other is highly undesirable, since it is detrimental to both reaction and condensation.

Therefore, it is very important that as few as possible of the first droplets collide with second droplets in their path through the reaction zone. It is believed that the smaller the droplets the less the chances to collide. Thus, if there is no other compelling reason to increase the size of the droplets, they should be made to be as small as possible, of course within reason. It is also preferable that regardless of the size of the first droplets, the size of the second droplets is maintained adequately smaller in a manner to reduce the probabilities of collision between first and second droplets.

The operation of this embodiment regarding internal inside condensation is substantially the same as described hereinabove for the embodiments of FIGS. 3 and 4, with the difference that the internal inside condensation takes place on the second droplets instead of the walls of the reaction chamber 22 or the coil 124, respectively.

A controlled reactor device or apparatus 320 of the present invention can be exemplified by the schematic diagram illustrated in FIG. 6. Although the internal inside condensation in the example of FIG. 6 is conducted by a set of second droplets, which is highly preferable as discussed hereinabove, substantially the same or similar elements and operation principles may be used, regardless of the type of means used for conducting said internal inside condensation.

The controlled reactor device 320 of FIG. 6 comprises a reaction chamber 322, which is provided with a first atomizer 328 and a second atomizer 328', preferably in the vicinity of the upper end 332 of the reactor 322. At the upper end 332, there is also a gas exit port 338 connected to a valve 339. In the vicinity of the lower end 342, there is provided a gas line 333 ending to one or more orifices 336. A liquid exit port 340 is also located in the vicinity of the lower end 342 of the reaction chamber 322.

One or more thermocouples 344, arranged within the reaction zone 334, are connected to a preferably computerized controller 346 through input lines 344i. The thermocouples 344 may be positioned in any appropriate places of the reaction zone 334 in order to monitor the temperature of the falling droplets at different distances between the upper end 332 and the lower end 442 of the reaction chamber 322, either continuously, or at predetermined intervals of time.

The device 320 is also provided with a source of first liquid, in the form of a tank 348, for example. A first pump 350 is adapted to pump a first stream of the first liquid from the tank 348 at a first controlled flow rate to a first heat exchanger 352, a first temperature monitor 354, a first flow rate monitor or first flow meter 356, and finally through first atomizer 328. In the same manner, a second pump 350' is adapted to pump a second stream of the first liquid from the tank 348 at a second controlled flow rate to a second heat exchanger 352', a second temperature monitor 354', a second flow rate monitor or second flow meter 356', and finally through the second atomizer 328'. The heat exchanger may also be a simple heater or a simple cooler or chiller, depending on the reaction to take place and the initial temperature of the first liquid from the tank 348. According to the present invention, a heat exchanger may be a conventional heat exchanger, a heater, a cooler or a chiller.

The first temperature monitor 354 and the first flow meter 356 are connected to the computerized controller 346 through input lines 354i and 356i, respectively for providing the computerized controller 346 with first temperature and first flow rate information, respectively. In the same manner, the second temperature monitor 354' and the second flow meter 356' are connected to the computerized controller 346 through input lines 354i' and 356i', respectively, for providing the computerized controller 346 with second temperature and second flow rate information, respectively.

There is also provided a gas source 358, which contains the second reactant, oxygen for example, in the case of oxidation of cyclohexane to adipic acid for example.

The second gas source 358 is connected to a pressurizing pump 360, which is connected to gas line 333, which in turn leads to the orifices 336 in the reaction chamber 322. Since the gas in most occasions is already pressurized in the gas source, which is usually a suitable tank, the pressurizing pump 360 may be replaced by a valve (not shown) or a pressure regulator (not shown), or both.

A pressure gauge 362 is also provided within the reaction chamber 322 in order to provide pressure information to the computerized controller 346 through input line 362'.

Carbon monoxide and carbon dioxide monitors (not shown) are also preferably provided to transfer respective information to the controller 346 as already discussed earlier.

The preferably computerized controller 346 controls the pumps 350 and 350' through output lines 350u and 350u', respectively, and the heat exchangers 352 and 352' through output lines 352u and 352u' respectively. It also controls the valve 339 and the pressurizing pump 360 through output lines 339u and 360u, respectively. As already mentioned, the pump 360 may be replaced by a valve or pressure regulator (not shown), in which case the valve or pressure regulator are controlled through line 360u in place of the pump 360.

In operation of the controlled reaction device, a first stream of the first liquid, which comprises for example a mixture of cyclohexane as first reactant, a solvent, such as acetic acid for example, a catalyst, such as a cobalt salt for example, an initiator, such as cyclohexanone or acetaldehyde for example, and other desirable adjuncts, in proportions which may be similar to the ones described in the art for conventional systems, is pumped from tank 348 by pump 350 through the heat exchanger 352, where it assumes a desired temperature, measured by the temperature monitor 354.

The heated first stream passes through the flow meter 356, where its flow rate is measured, and then, it enters the reaction chamber through the first atomizer 328 and nozzles 330 in the form of atomized or sprayed first droplets at the first atomization temperature as measured by the temperature monitor 354. Both the first atomization temperature and the first flow rate are provided to the controller 346 for processing. If the temperature provided to the controller 346 is higher than the desired atomization temperature, the heat exchanger 352 is ordered by the controller 346, through output line 352u, to provide less heat to the first stream passing through the heat exchanger, until the first atomization temperature drops to the desired level. If the temperature provided to the controller 346 is lower than the desired atomization temperature, the heat exchanger 352 is ordered by the controller 346, through output line 352u, to provide more heat to the first stream passing through the heat exchanger 352, until the first atomization temperature increases to the desired level.

Similarly, if the flow rate as measured by the flow meter 356 and provided to the controller 346 is higher than the desired first flow rate, the pump 350 is ordered by the controller 346, through output line 350u, to lower its pumping action, until the first flow rate drops to the desired level. If the flow rate as measured by the flow meter 356 and provided to the controller 346 is lower than the desired first flow rate, the pump 350 is ordered by the controller 346, through output line 350u, to raise its pumping action, until the first flow rate increases to the desired level.

A second stream of the first liquid, is also pumped from tank 348 by pump 350' through the heat exchanger 352', where it assumes a desired second atomization temperature, lower than the atomization temperature of the first stream and measured by the temperature monitor 354'.

The heated second stream passes through the flow meter 356', where its flow rate is measured, and the then, it enters the reaction chamber through the second atomizer 328' and nozzles 330' in the form of atomized or sprayed second droplets at the second atomization temperature (lower than the first atomization temperature) as measured by the temperature monitor 354'. Both the second atomization temperature and the second flow rate are provided to the controller 346 for processing. If the temperature provided to the controller 346 is higher than the desired second atomization temperature, the heat exchanger 352' is ordered by the controller 346, through output line 352u', to provide less heat to the second stream passing through the heat exchanger 352', until the second atomization temperature drops to the desired level. If the temperature provided to the controller 346 is lower than the desired second atomization temperature, the heat exchanger 352' is ordered by the controller 346, through output line 352u', to provide more heat to the second stream passing through the heat exchanger 352', until the second atomization temperature increases to the desired level.

Similarly, if the flow rate as measured by the flow meter 356' and provided to the controller 346 is higher than the desired second flow rate, the pump 350' is ordered by the controller 346, through output line 350u', to lower its pumping action, until the second flow rate drops to the desired level. If the flow rate as measured by the flow meter 356' and provided to the controller 346 is lower than the desired second flow rate, the pump 350' is ordered by the controller 346, through output line 350u', to raise its pumping action, until the second flow rate increases to the desired level.

At the same time that the first and second atomizations are taking place, a gas containing a second reactant, such as oxygen for example, enters the system though gas line 333 and the orifices 336, and moves in a substantially opposite direction than the first and second droplets. The pressure in the reaction chamber 322 is measured by the pressure gauge 362, and the information is fed to the computerized controller 346 through input line 362'. If the pressure is higher than a desired pressure, the controller orders the valve 339 to assume a more open position, or it orders the pressurizing pump to reduce feeding of gas to line 333, until the pressure assumes the desired value. Since waste minimization is a very important factor for environmental improvement, the computerized controller is preferably programmed in a manner that larger opening of the valve 339 is used as a last resort. If the pressure is lower than the desired one, the controller 346 orders the valve 339 to assume a more closed position or the pump 360 to pass more gas to line 333 from the gas source 336. The flow of the gas through line 333 may be measured by a flow meter (not shown) on said line and fed to the computerized controller 346. It becomes then clear that the pressure in the reaction chamber and flow rate of gas to the reaction chamber can be controlled by adjusting the pumping action of the pressurizing pump 360 and the opening of valve 339. As aforementioned, the pressurizing pump 333 may be replaced by other devices, such as a pressure regulator for example, if the pressure in the gas source 358 is maintained at a suitable pressure greater or equal to the desired pressure in the reaction chamber 322.

In case it is desired to remove inert gases, the opening of valve 339 may be increased. Simultaneously, if so desired, second reactant, for example oxygen, may be forced into the reaction chamber in order to maintain both the total pressure and the partial pressure of the second reactant at predetermined levels. A monitor (not shown) for second reactant may be positioned within the off-gas region to monitor the content of second reactant. This information, combined with the known amounts of second reactant entering the reaction chamber, may be easily correlated to the progress of the reaction, by simple mathematical techniques well known to the art, and easily performed by the computerized controller 346.

As the droplets proceed within the reaction zone 334 from the upper part 332 toward the lower end 342 of the reaction chamber 322, the second reactant, oxygen for example, reacts at least partially with the first reactant, cyclohexane for example. During the reaction, heat is generated, which raises the temperature of the first droplets. As the temperature of the first droplets rises, evaporation of first liquid or components thereof takes place. As aforementioned, the rate of evaporation may be controlled by adjusting the rate of condensation of vapors on the second droplets, the temperature of which is lower. By increasing the second flow rate (the flow rate of the second stream) and decreasing the second atomization temperature, the rate of condensation of vapors on the second droplets increases, resulting in an increase of vaporization rate from the first droplets, which in turn results in cooling of the first droplets. By decreasing the second flow rate (the flow rate of the second stream) and increasing the second atomization temperature, the rate of condensation of vapors on the second droplets decreases, resulting in an decrease of vaporization rate from the first droplets, which in turn results in reduced cooling of the first droplets.

It can be seen then that heat transfer from the first droplets to the second droplets or any other condensation means is regulated by the controller 346. The vapor condensation, of vapors formed from the first droplets, on the second droplets may be at least partially controlled by one parameter selected from a group consisting of (a) temperature difference between the first and the second atomization temperature, (b) flow rate difference between the first and the second flow rate (c) the volatiles content of the first liquid, (d) the volatiles content of the second liquid, (e) the volatility of the first or second volatiles, and (f) a combination thereof.

It is preferable that the total amount of second reactant allowed to enter the reaction chamber 322 is in the range corresponding to one time stoichiometric to five times stoichiometric, and preferably to two times stoichiometric, with respect to the total amount of the first reactant fed to the reaction chamber or reaction zone. This is very important for waste minimization and environmental improvement reasons, since the off gases produced under these conditions are minimized. In one example, if X moles of first reactant, such as cyclohexane for example, exist in an unreacted state in a reactor to form adipic acid by direct oxidation with oxygen, then preferably 2.5X to 12.5X, and more preferably 2.5X to 5X moles of oxygen are allowed to be present in the reactor, regardless of whether the reaction is a batch reaction or a continuous reaction.

The thermocouples 344 take the temperature of the droplets and feed this information to the controller 346. In one embodiment of the present invention, the controller may order the pump 350' to interrupt pumping at certain predetermined intervals and for short periods of time. When this occurs, there are no second droplets in the reaction chamber, and therefore, the thermocouples directly measure the actual temperature of the first droplets in substantially the absence of condensation, as the first droplets proceed in the reaction zone 334 from the upper end 332 to the lower end 342 of the reaction chamber 322. If the interruption of the second droplet flow is of sufficiently short duration, the first droplets will continue to be cooled by the solvent vaporization effect, and the temperature measured by the controller under these circumstances represents the actual temperature that the first droplets attain due to the combined effects of heat released by the reaction and solvent evaporation, when the rest of the parameters remain constant. //If the interruption is allowed to continue for a sufficiently longer period of time, then the temperature measured by the controller represents the maximum temperature that the first droplets may attain due to the heat released by the reaction, when the rest of the parameters remain constant. The controller, based on this information, gives appropriate orders to the other components of the device to prevent this temperature from exceeding predetermined limits, if so desired, not only for purposes of controlling the reaction but also to prevent catastrophic results in case that the internal condensation is interrupted for prolonged periods of time by accident or otherwise, and the reaction heat released is excessive. This presents an additional safeguard.

Although one thermocouple, preferably close to the lower end 342, may be used for monitoring temperature, it is more preferable to use more than one thermocouples 344 in the reaction zone 334 for determining the rate of temperature rise, or temperature profile in the droplet path. This is useful information, since, based on such information, the elevation of the second atomizer may be physically lowered to the point where the internal inside condensation is needed most. Also the controller 346 is preferably adapted to utilize data concerning temperature profiles in the reaction chamber in order to regulate the flow rates, atomization temperatures of the first and the second liquids, as well as other parameters as discussed hereinbelow. The higher the temperature changes from thermocouple to thermocouple the more drastic the changes ordered by the controller.

Pressure inside the reaction chamber may influence the rates of evaporation and condensation, and thus it may be used by the controller 346, especially in combination with other parameters already discussed, to control the heat exchange between the first and second droplets. Lower pressure causes higher evaporation rate, while higher pressure causes lower evaporation rate, provided that the vapors are condensed.

The first and second droplets preferably coalesce together into a mass of liquid 364, which exits the reactor through liquid exit port 340. Depending on the degree of completion of the reaction, the liquid 364 may be re-circulated into the tank 348, preferably after at least partial removal of the reaction product, or undergo other treatment, depending on the reaction.

The miscellaneous control parameters according to the preferred embodiments of the instant invention are used in a way that condensation is controlled in a manner that in turn the conversion of the first reactant in the first droplets, the temperature of the first droplets, and the final composition of the first droplets may be controlled at one or more predetermined points within the reactor.

There are mainly two aspects to first reactant conversion control. The first is to determine the first reactant conversion as a function of its path through the reactor, while the second is to control the first reactant conversion at a desired setpoint or setpoints. The amount of reaction in the first droplet and the amount of first reactant conversion, as a function of the first droplets path through the reactor, may be calculated by the computerized controller 346—using mass and energy balances well known to the art—as a function of:

- the overall temperature of the combined first and second droplets at a certain point or points within the reactor as determined by one or more of the thermocouples 344;
- first stream inlet flowrate as measured by first flowmeter 356, first atomization temperature as measured by the first temperature monitor 354, and composition as determined to be in tank 348, either because of mixing known materials in known amounts, or by analytical techniques well known to the art, or composition as modified in the first stream by introduction of desired ingredients through other streams (not shown);
- second stream inlet flowrate as measured by second flowmeter 356', second atomization temperature as measured by the second temperature monitor 354', and composition as determined to be in tank 348, either because of mixing known materials in known amounts, or by analytical techniques well known to the art, or composition as modified in the second stream by introduction of desired ingredients through other streams (not shown);

reactor pressure as measured by the pressure gauge 362; and the concentrations of inert gases, if present, and second reactant, such as oxygen for example, in the reactor.

The first reactant conversion may also be directly measured by sample analysis.

The first reactant conversion may then be controlled by the following guidelines (implemented alone or in concert by controller 346 and the corresponding control devices):

conversion can be decreased by decreasing the first atomization temperature through the first heat exchanger 352;

conversion can be decreased by decreasing second atomization temperature through the second heat exchanger 352'; this increases condensation on the second droplets, increasing vaporization from the first droplets resulting in lowering the temperature of the first droplets, and therefore, in decreasing conversion;

conversion can be decreased by decreasing catalyst concentration; this can be done, for example, by introducing into the first stream a third stream (not shown), also controlled by the controller 346, containing all the ingredients of the contents of the tank 348, with lower content of catalyst or no catalyst; alternatively, in another example, the tank 348 can contain substantially all ingredients except catalyst and the third stream (not shown), also controlled by the controller 346, can contain substantially only catalyst, preferably dissolved in a liquid medium, so that controller 346 can change appropriately the flow of the third stream;

conversion can be decreased by increasing the concentration of the first reactant in the first liquid; this can be done, for example, by introducing into the second stream a fourth stream (not shown), also controlled by the controller 346, containing all the ingredients of the contents of the tank 348, but having higher content of first reactant; alternatively, in another example, the tank 348 can contain substantially all ingredients except first reactant and the fourth stream (not shown), also controlled by the controller 346, can contain substantially only first reactant, so that controller 346 can change appropriately the flow of the fourth stream;

conversion can be decreased by increasing the concentration of volatiles in the first stream; evaporation of volatiles decreases the temperature resulting in lower conversion; also dilution due to volatiles introduction leads to lower conversion; incorporation of controlled amounts of volatiles may be achieved by a fifth stream (not shown) entering into the first stream and controlled by the computerized controller 346;

conversion can be decreased by decreasing second reactant concentration in the reactor; this can be achieved, for example, by introducing into line 333 an amount of inerts controlled (not shown) by the computerized controller 346; or it can be achieved, in another example, by decreasing the pumping action of the pressurizing pump 360, or increasing the opening of valve 339, or a combination thereof;

conversion can be decreased by increasing first liquid droplet size through control (not shown) of the first atomizer by the controller 346, using methods well known to the art.

The converse of these guidelines is also true.

It becomes evident then that the desired values of conversion or transient conversion depend on a number of parameters, and can vary broadly in each particular case. For example, in some occasions, values of transient conversion may go as low as 0.05% or even lower. This is true not only in the context of the present invention, but also in the context of our co-pending applications Ser. Nos. 08/477,234, 08/478,257, 08/477,195, and 08/475,340, all of which were filed on Jun. 7, 1995.

There are two aspects to first droplet temperature control. The first is to determine the temperature of the first droplet as a function of its path through the reactor. The second is to control the temperature at a desired setpoint or setpoints.

The first droplet temperature, as a function of its path through the reactor, can be calculated as a function of the following variables:

amount of first reactant conversion having taken place in the first droplet as a function of its path through the reactor as calculated by the computerized controlled 346 or as measured by sample analysis;

first stream inlet flowrate as measured by the first flowmeter 356, first atomization temperature as measured by the first temperature monitor 354, the average temperature between the first and second droplets as measured by the thermocouples 344, and the composition in the tank 348, as made or as modified otherwise in the first stream;

second stream inlet flowrate as measured by the second flowmeter 356', second atomization temperature as measured by the second temperature monitor 354', the average temperature between the first and second droplets as measured by the thermocouples 344, and the composition in the tank 348, as made or as modified otherwise in the second stream;

reactor pressure as measured by the pressure gauge 362; and the concentrations of inerts and oxygen in the reactor as computed by the computerized controller 346, or as measured by direct analysis Given this information, the temperature of the first droplet, at a point or points within the reactor, may be calculated by the computerized controller 346 using mass balances, energy balances, vapor-liquid equilibrium data, and kinetic rate equations for mass and energy transfer well known to the art.

First droplet temperature may then be controlled by the following guidelines (implemented alone or in concert by the computerized controller 346):

the first droplet temperature can be decreased by decreasing first atomization temperature as measured by the first temperature monitor 354;

the first droplet temperature can be decreased by decreasing second atomization temperature as measured by the second temperature monitor 354;

the first droplet temperature can be decreased by decreasing catalyst concentration; this can be done, for example, by introducing into the first stream a third stream (not shown), also controlled by the controller 346, containing all the ingredients of the contents of the tank 348, with lower content of catalyst or no catalyst; alternatively, in another example, the tank 348 can contain substantially all ingredients except catalyst and the third stream (not shown), also controlled by the controller 346, can contain substantially only catalyst, preferably dissolved in a liquid medium, so that controller 346 can change appropriately the flow of the third stream;

the first droplet temperature can be decreased by decreasing the concentration of the first reactant in the first liquid; this can be done, for example, by introducing into the second stream a fourth (not shown) stream, also controlled by the controller 346, containing all the ingredients of the contents of the tank 348, with lower content or no first reactant; alternatively, in another example, the tank 348 can contain substantially all ingredients except first reactant and the fourth stream (not shown), also controlled by the controller 346, can contain substantially first reactant, so that controller 346 can change appropriately the flow of the fourth stream;

the first droplet temperature can be decreased by increasing the concentration of volatiles in the first stream; evaporation of volatiles decreases the temperature; incorporation of controlled amounts of volatiles may be achieved by the fifth stream (not shown) entering into the first stream and controlled by the computerized controller 346;

the first droplet temperature can be decreased by decreasing second reactant concentration in the reactor; this can be achieved, for example, by introducing into line 333 an amount of inerts controlled (not shown) by the computerized controller 346; or it can be achieved, in another example, by decreasing the pumping action of the pressurizing pump 360, or increasing the opening of valve 339, or a combination thereof;

the first droplet temperature can be decreased by increasing first liquid droplet size through control (not shown) of the first atomizer by the controller 346, using methods well known to the art.

The converse of these methods is also true.

There are two aspects to first droplet composition control. The first is to determine the composition of the first droplet as a function of its path through the reactor. The second is to control the composition of a selected ingredient, or of a group of selected ingredients which together form a subset of all the ingredients present in the droplet, at a desired value or values.

The first droplet composition, as a function of its path through the reactor, can be calculated as a function of the following variables:

amount of first reactant conversion having taken place in the first droplet as a function of its path through the reactor as calculated by the computerized controlled 346 or as measured by sample analysis;

first stream inlet flowrate as measured by the first flowmeter 356, first atomization temperature as measured by the first temperature monitor 354, the average temperature between the first and second droplets as measured by the thermocouples 344, and the composition in the tank 348, as made or as modified otherwise in the first stream;

second stream inlet flowrate as measured by the second flowmeter 356', second atomization temperature as measured by the second temperature monitor 354', the average temperature between the first and second droplets as measured by the thermocouples 344, and the composition in the tank 348, as made or as modified otherwise in the second stream;

reactor pressure as measured by the pressure gauge 362; and the concentrations of inerts and oxygen in the reactor as computed by the computerized controller 346, or as measured by direct analysis;

temperature of the first droplet as a function of its path through the reactor

Given this information, the composition of the first droplet, at a point or points within the reactor, may be calculated using mass balances, energy balances, vapor-liquid equilibrium data, and kinetic rate equations for mass and energy transfer well known to the art.

First droplet composition of a selected ingredient, or of a group of selected ingredients which together form a subset of all the ingredients present in the droplet, may be controlled at a desired value or values by the following guidelines (implemented alone or in concert):

Content of first reactant can be decreased by increasing first atomization temperature as described above;

Content of first reactant can be decreased by decreasing second atomization temperature as described above;

Content of first reactant can be decreased by increasing catalyst concentration as described above;

Content of first reactant can be decreased by decreasing the concentration of the first reactant in the first liquid, or the first stream or the second stream or a combination thereof, as described above;

content of first reactant can be decreased by decreasing the concentration of volatiles in the first liquid as described above;

content of first reactant can be decreased by increasing second reactant concentration in the reactor as described above;

content of first reactant can be decreased by decreasing first liquid droplet size as described above;

content of volatiles can be decreased by increasing first atomization temperature as described above;

content of volatiles can be decreased by decreasing second atomization temperature as described above;

content of volatiles can be decreased by increasing catalyst concentration in the first stream as described above;

content of volatiles can be decreased by increasing the concentration of the first reactant in the first stream as described above;

content of volatiles can be decreased by decreasing the concentration of volatiles in the first stream as described above;

content of volatiles can be decreased by increasing second reactant concentration in the reactor as described above; and content of volatiles can be decreased by decreasing first droplet size as described above.

The converse of these methods is also true.

It should be stressed that when the internal inside condensation is performed by solid surfaces within the reaction chamber, and not by means of second droplets, the first droplet temperature can be directly measured by thermocouples positioned in desired locations of the reaction chamber.

The use of second droplets, however, for condensation is of utmost importance, since it presents an unprecedented way of ultra-efficient manner to control condensation within the reaction zone, in an exothermic reaction.

The second liquid may have the same composition as the first liquid, as described above where it is in the form of a second stream of the first liquid, or it may have a different composition. It is highly preferable that it has the same composition. It may also have such a composition so that the mass of the liquid 364 after at least partial removal of the reaction product assumes a composition similar to the composition of the first liquid. For example, in the case of oxidation of cyclohexane to adipic acid, the second liquid may contain an excess of cyclohexane, which will virtually replace in liquid mass 364 the cyclohexane which will react in the first liquid. Absence of catalyst in the second liquid promotes absence of reaction in the second droplets. The second liquid may also be immiscible with the first liquid, so that they may be separated easily after removal from the reaction chamber. Nevertheless, close similarity of the first and second liquids, highly simplifies the process, and as aforementioned, it is highly preferable.

In a different embodiment of the present invention, better shown in FIG. 7, the reactor 422 comprises a first atomizer 428, and a ring 428', which is adapted to distribute the second liquid substantially uniformly on the inside surface of the reactor 422 in the form of a thick film or curtain 466. The second liquid has a lower temperature than the first liquid, and condensation of vapors produced by the first droplets takes place on the curtain of said second liquid which covers the periphery of the reaction zone.

The operation of this embodiment is substantially the same as the operation of the previous embodiments, with the difference that the vapors produced by the first droplets condense on the curtain or thick film 446.

In still a different embodiment of the present invention, better shown in FIG. 8, the reactor 522 comprises a first atomizer 528, and a ring 528', which is adapted to distribute the second liquid substantially uniformly on the inside surface of the reactor 522 in the form of a thick film or curtain 566, as in the case of the previous embodiment. The second liquid has a lower temperature than the first liquid, and condensation of vapors produced by the first droplets takes place on the curtain of said second liquid which covers the periphery of the reaction zone. At the lower end 542 of the reactor 522 there is provided a pan 568, ending to a pan exit 570, while the reaction chamber 522 ends to a reactor exit 572.

The operation of this embodiment is substantially the same as the operation of the previous embodiment, with the difference that most of the reacted material falls into the pan and removed from the pan exit 570, while most of the condensed material is removed from the reactor exit 572. This at least partial separation of reacted material from condensed material is important, especially when the composition of the curtain 566 differs substantially from the composition of the first liquid.

Figure 9:
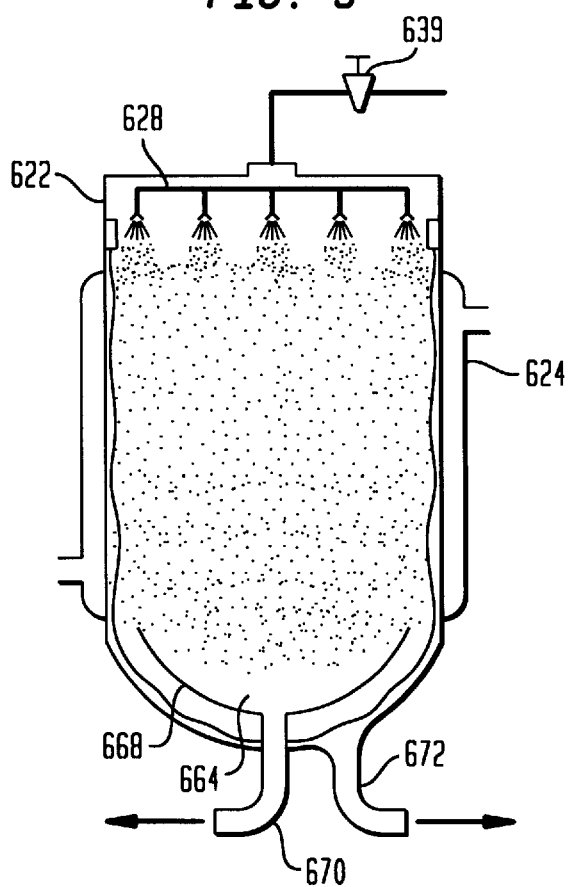
FIG. 9 illustrates schematically still another preferred embodiment of the present invention, wherein the condensation takes place on a solid surface surrounding the reaction zone, and wherein condensed material is at least partially separated from reacted material.

In still a different embodiment, better shown in FIG. 9, there is provided a jacket 624, similar to the jacket 24 of the embodiment depicted in FIG. 3. The jacket 624 provides a cold solid surface in the reactor 622, on which surface vapors are condensed and are removed through the reactor exit 672, while most of the reacted material is removed from the fan exit 670 after being collected by pan 668.

The operation of this embodiment is substantially the same as the operation of the immediately previous embodiment.

As aforementioned, the methods and the devices of the instant invention may be used for substantially any types of exothermic reactions, wherein a first reactant in a liquid reacts with a second reactant in a gas to form a reaction product. Such reactions include, but are not limited to esterifications, ether formations, amide or imide formations, salt formations, ammoniations, nitrations, oxidations, and the like. Oxidations are particularly suitable for oxidation reactions of organic compounds, wherein the major portion of the reaction product is an oxidation product different than $CO$, $CO_2$, or a mixture thereof. One of the reasons why this is so, is that, due to the intricate criticalities of the present invention, the reaction rates, reaction homogeneity, yield, and other important properties are considerably improved, while in the absence of said criticalities complete oxidation to $CO/CO_2$ would take place. Actually, the same conditions of atomization without said criticalities, are presently used in combustion engines of automobiles and other devices, to substantially completely oxidize (combust or burn in other words) organic compounds such as gasoline to a mixture of $CO/CO_2$.

In contrast, according to the present invention, if for example, the first reactant is cyclohexane, the major portion of the oxidation product may be substantially cyclohexanol, cyclohexanone, cyclohexylhydroperoxide, caprolactone, adipic acid, the like, and mixtures thereof. Organic acids are preferable oxidation products.

Many catalysts used for reactions, such as oxidations for example, are transition metals having more than one valence states. Their major catalytic action is exhibited when they are at a higher valance state than their lowest valance state at which they exist as ions. One good example is cobalt in the case of oxidation of cyclohexane to adipic acid. An initiation period before the oxidation starts has often been attributed by researches to the addition of cobalt ions at a valance state of II. The cobalt catalyst is added at valance state II because cobaltous acetate, for example, is more readily available and it is less expensive than cobaltic acetate. Thus, it takes a period of time for the cobaltous ion to be oxidized to cobaltic ion and start acting as a catalyst according to methods in the art so far, unless cobalt II is used, or the cobalt II is preoxidized. Even then, it takes time to oxidize cobalt II to cobalt III ions, due to the small interface provided by bubbling the gas through the solution.

In the case of the instant invention, this period of oxidation becomes considerably smaller because of the high interfacial surface area provided relative to liquid mass in the reaction chamber as atomized first droplets. In addition, the cobaltous ion can be pre-oxidized.

As aforementioned, reactions, such as oxidations for example, according to this invention, are non-destructive oxidations, wherein the oxidation product is different than carbon monoxide, carbon dioxide, and a mixture thereof. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane;

preparation of $C_5$–$C_8$ aliphatic dibasic acids from the corresponding ketones, alcohols, and hydroperoxides of saturated cycloaliphatic hydrocarbons, such as for example preparation of adipic acid from cyclohexanone, cyclohexanol, and cyclohexylhydroperoxide;

preparation of $C_5$–$C_8$ cyclic ketones, alcohols, and hydroperoxides from the corresponding saturated cycloaliphatic hydrocarbons, such as for example preparation of cyclohexanone, cyclohexanol, and cyclohexylhydroperoxide from cyclohexane; and preparation of aromatic multi-acids from the corresponding multi-alkyl aromatic compounds, such as for example preparation of phthalic acid, isophthalic acid, and terephthalic acid from o-xylene, m-xylene and p-xylene, respectively.

Regarding adipic acid, the preparation of which is especially suited to the methods and devices or apparatuses of this invention, general information may be found in a plethora of U.S. Patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; 5,321,157; and 5,463,119.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. Although this invention has been mainly exemplified with oxidation process, any exothermic reaction between a liquid and a gas (under the conditions of the reaction) is includes in the realm of the instant invention. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

In the different figures of the drawing, numerals differing by 100 represent elements which are either substantially the same or perform the same function. Therefore, in the case that one element has been defined once in a certain embodiment, its re-definition in other embodiments illustrated in the figures by the same numerals or numerals differing by 100 is not necessary, and it has been often omitted in the above description for purposes of brevity.

The words "inlet line" and "outlet line" are used to signify lines adapted to transfer materials for the operation of the process, such as volatiles, reaction products, off-gases, and the like, for example. The words "input line" and "output line" have been used to signify lines adapted to transmit signals, which are mostly electrical, but they can also be hydraulic, pneumatic, optical, acoustic, and the like, for example.

A diagonal arrow through an element denotes that the element is controlled though a line, preferably electrical, connected to the arrow.

Internal condensation according to this invention is condensation of condensibles, which takes place within the pressurized system and before pressure drop to about atmospheric pressure. Inside condensation or inside internal condensation is condensation which takes place within the reaction chamber.

Condensibles are substances having a boiling point higher than 15° C., while non condensibles are substances that have a boiling point of 15° C. and lower. It should be understood that when referring to condensibles, it is meant "mostly condensibles" and when referring to non-condensibles it is meant "mostly non-condensibles", since small amounts of one kind will be mixed with the other kind at substantially all times.

In cases where dilution or concentration of the droplets occurs as they travel from the atomizer to the sample collector, such dilution has to be taken into account in the calculation performed by the computerized controller by monitoring the sources of dilution or concentration and using well known to the art techniques.

Response time between changing one variable or parameter and the result it brings about should also be taken into account, and the controller should be calibrated or programmed accordingly, by well known to the art techniques.

What is claimed is:

1. A method of making a reaction product different than carbon monoxide or carbon dioxide in a reaction zone by reacting a first reactant contained in a first liquid with a second reactant contained in a gas, the first reactant and the second reactant characterized by an ability to react with each other in an exothermic manner, the method comprising the steps of:

atomizing the first liquid to form a plurality of first droplets having an average droplet size in the gas at a first flow rate, at a first atomization temperature, and at a reaction pressure;

reacting at least partially the first reactant with the second reactant to form the reaction product and release heat;

evaporating at least part of the first liquid, thereby removing at least a portion of the released heat; and restricting the portion of removed heat within predetermined limits by causing controlled condensation within the reaction zone.

2. A method as defined in claim 1, wherein the controlled condensation is caused by a second liquid atomized in the form of second droplets having a second average droplet size within the reaction zone.

3. A method as defined in claim 2, wherein the second liquid contains volatiles at a desired content and a desired volatility, and enters the reaction zone under a condition selected from a group consisting of a second flow rate, a second atomization temperature, and a combination thereof, the second atomization temperature being lower than the first atomization temperature.

4. A method as defined in claim 3, wherein the first liquid contains volatiles at a desired content a desired volatility, and wherein the condensation is at least partially controlled by one parameter selected from a group consisting of (a) temperature difference between the first and the second atomization temperature, (b) flow rate difference between the first and the second flow rate (c) the volatiles content of the first liquid, (d) the volatiles content of the second liquid, (e) the volatility of the first or second volatiles, and (f) a combination thereof.

5. A method as defined in claim 1, wherein the condensation is controlled by changing the reaction pressure.

6. A method as defined in claim 2, wherein the first liquid comprises a first set of ingredients, and the second liquid comprises a second set of ingredients, the first set and the second set having at least one common ingredient.

7. A method as defined in claim 6, wherein the first set and the second set comprise substantially the same ingredients.

8. A method as defined in claim 6, wherein the first set and the second set comprise substantially the same ingredients, substantially under the same proportions.

9. A method as defined in claim 6, wherein the first set and the second set consist of substantially the same ingredients, substantially under the same proportions.

10. A method as defined in claim 4, wherein the first liquid comprises a first set of ingredients, and the second liquid comprises a second set of ingredients, the first set and the second set having at least one common ingredient.

11. A method as defined in claim 10, wherein the first set and the second set comprise substantially the same ingredients.

12. A method as defined in claim 10, wherein the first set and the second set consist of substantially the same ingredients, substantially under the same proportions.

13. A method as defined in claim 1, wherein the controlled condensation is caused by a solid surface within the reaction zone.

14. A method as defined in claim 1, wherein the controlled condensation is caused by a solid surface in the periphery of the reaction zone.

15. A method as defined in claim 14, further comprising a step of at least partially separating condensed material from reacted material.

16. A method as defined in claim 1, wherein the controlled condensation is caused by a liquid surface in the periphery of the reaction zone.

17. A method as defined in claim 16, further comprising a step of at least partially separating condensed material from reacted material.

18. A method as defined in claim 1, wherein the first reactant comprises a compound selected from a group consisting of cyclohexane, cyclohexanone, cyclohexanol, cyclohexylhydroperoxide, o-xylene, p-xylene, m-xylene, a mixture of at least two of cyclohexane, cyclohexanone, cyclohexanol, and cyclohexylhydroperoxide, and a mixture of at least two of o-xylene, p-xylene, and m-xylene;

the second reactant comprises oxygen; and the reaction product comprises a compound selected from a group consisting of cyclohexanone, cyclohexanol, cyclohexylhydroperoxide, adipic acid, phthalic acid, isophthalic acid, terephthalic acid, a mixture of at least two of cyclohexanone, cyclohexanol, and cyclohexylhydroperoxide, and a mixture of at least two of phthalic acid, isophthalic acid, and terephthalic acid.

19. A method as defined in claim 4, wherein the first reactant comprises a compound selected from a group consisting of cyclohexane, cyclohexanone, cyclohexanol, cyclohexylhydroperoxide, o-xylene, p-xylene, m-xylene, a mixture of at least two of cyclohexane, cyclohexanone, cyclohexanol, and cyclohexylhydroperoxide, and a mixture of at least two of o-xylene, p-xylene, and m-xylene;

the second reactant comprises oxygen; and the reaction product comprises a compound selected from a group consisting of cyclohexanone, cyclohexanol, cyclohexylhydroperoxide, adipic acid, phthalic acid, isophthalic acid, terephthalic acid, a mixture of at least two of cyclohexanone, cyclohexanol, and cyclohexylhydroperoxide, and a mixture of at least two of phthalic acid, isophthalic acid, and terephthalic acid.

20. A method as defined in claim 12, wherein the first reactant comprises a compound selected from a group consisting of cyclohexane, cyclohexanone, cyclohexanol, cyclohexylhydroperoxide, o-xylene, p-xylene, m-xylene, a mixture of at least two of cyclohexane, cyclohexanone, cyclohexanol, and cyclohexylhydroperoxide, and a mixture of at least two of o-xylene, p-xylene, and m-xylene;

the second reactant comprises oxygen; and the reaction product comprises a compound selected from a group consisting of cyclohexanone, cyclohexanol, cyclohexylhydroperoxide, adipic acid, phthalic acid, isophthalic acid, terephthalic acid, a mixture of at least two of cyclohexanone, cyclohexanol, and cyclohexylhydroperoxide, and a mixture of at least two of phthalic acid, isophthalic acid, and terephthalic acid.

21. A method of making a reaction product different than carbon monoxide or carbon dioxide by reacting a first reactant contained in a first liquid with a second reactant contained in a gas, the first reactant and the second reactant characterized by an ability to react with each other in an exothermic manner, the method comprising the steps of:

dividing the first liquid into a first stream and to a second stream;

causing the first stream to have a first atomization temperature and the second stream to have a second atomization temperature lower than the first atomization temperature;

atomizing the first stream to form a plurality of first droplets in the gas at a first flow rate and at the first atomization temperature;

atomizing the second stream to form a plurality of second droplets in the gas at a second flow rate and at the second atomization temperature;

reacting at least partially the first reactant in the first droplets with the second reactant to form the reaction product and release heat; and maintaining first droplet temperature within predetermined limits by evaporation of at least part of the first liquid from the first droplets, and condensation of at least part of the evaporated first liquid o n the second droplets.

22. A method as defined in claim 21, wherein the condensation is at least partially controlled by one parameter selected from a group consisting of (a) temperature difference between the first and the second atomization temperature, (b) flow rate difference between the first and the second flow rate (c) the volatiles content of the first liquid, (d) the volatiles content of the second liquid, (e) the volatility of the first or second volatiles, and (f) a combination thereof.

23. A method as defined in claim 22, wherein the first reactant comprises a compound selected from a group consisting of cyclohexane, cyclohexanone, cyclohexanol, cyclohexylhydroperoxide, o-xylene, p-xylene, m-xylene, a mixture of at least two of cyclohexane, cyclohexanone, cyclohexanol, and cyclohexylhydroperoxide, and a mixture of at least two of o-xylene, p-xylene, and m-xylene;

the second reactant comprises oxygen; and the reaction product comprises a compound selected from a group consisting of cyclohexanone, cyclohexanol, cyclohexylhydroperoxide, adipic acid, phthalic acid, isophthalic acid, terephthalic acid, a mixture of at least two of cyclohexanone, cyclohexanol, and cyclohexylhydroperoxide, and a mixture of at least two of phthalic acid, isophthalic acid, and terephthalic acid.

24. A method of making a reaction product different than carbon monoxide or carbon dioxide by reacting a first reactant contained in a first liquid with a second reactant contained in a gas, the first reactant and the second reactant characterized by an ability to react with each other in an exothermic manner, the method comprising the steps of:

dividing the first liquid into a first stream and to a second stream;

causing the first stream to have a first atomization temperature and the second stream to have a second atomization temperature lower than the first atomization temperature;

atomizing the first stream to form a plurality of first droplets in the gas at a first flow rate and at the first atomization temperature;

atomizing the second stream to form a plurality of second droplets in the gas at a second flow rate and at the second atomization temperature;

reacting at least partially the first reactant in the first droplets with the second reactant to form the reaction product and release heat; and maintaining first droplet temperature within predetermined limits by transferring heat from the first droplets to the second droplets.

25. A method as defined in claim 24, wherein the heat transfer comprises a step of controlling condensation on the second droplets, which condensation is at least partially controlled by one parameter selected from a group consisting of (a) temperature difference between the first and the second atomization temperature, (b) flow rate difference between the first and the second flow rate (c) the volatiles content of the first liquid, (d) the volatiles content of the second liquid, (e) the volatility of the first or second volatiles, and (f) a combination thereof.

26. A method as defined in claim 1, wherein a total amount of second reactant is fed to the reaction zone, the total amount of second reactant being in a range corresponding to one time stoichiometric to two times stoichiometric with respect to a total amount of first reactant fed to the reaction zone.

27. A method as defined in claim 2, wherein a total amount of second reactant is fed to the reaction zone, the total amount of second reactant being in a range corresponding to one time stoichiometric to two times stoichiometric with respect to a total amount of first reactant fed to the reaction zone.

28. A method as defined in claim 4, wherein a total amount of second reactant is fed to the reaction zone, the total amount of second reactant being in a range corresponding to one time stoichiometric to two times stoichiometric with respect to a total amount of first reactant fed to the reaction zone.

29. A method as defined in claim 20, wherein a total amount of second reactant is fed to the reaction zone, the total amount of second reactant being in a range corresponding to one time stoichiometric to two times stoichiometric with respect to a total amount of first reactant fed to the reaction zone.

30. A method as defined in claim 21, wherein a total amount of second reactant is fed to the reaction zone, the total amount of second reactant being in a range corresponding to one time stoichiometric to two times stoichiometric with respect to a total amount of first reactant fed to the reaction zone.

31. A method as defined in claim 24, wherein a total amount of second reactant is fed to the reaction zone, the total amount of second reactant being in a range corresponding to one time stoichiometric to two times stoichiometric with respect to a total amount of first reactant fed to the reaction zone.

32. A method as defined in claim 19, wherein the first liquid contains a catalyst at a desired concentration, the first and second reactants are characterized by desired concentrations, the exothermic reaction is characterized by a conversion of the first reactant to reaction product, the exothermic reaction takes place in a reaction zone, the first droplets have a path within said reaction zone, said first droplets have a temperature as function of their path through the reaction zone, wherein the second droplets have also a path through the reaction zone, and wherein said conversion is controlled by a parameter selected from a group consisting of:

changing the first atomization temperature;
changing the second atomization temperature;
changing the catalyst concentration;
changing the first reactant concentration in the first liquid;
changing the volatiles content in the first liquid;
changing the volatiles content in the second liquid;
changing the second reactant concentration;
changing the average droplet size of the first liquid; and
a combination thereof; and wherein said first droplet temperature is controlled by a parameter selected from a group consisting of:
changing the first atomization temperature;
changing the second atomization temperature;
changing the catalyst concentration;
changing the first reactant concentration;
changing the volatiles content in the first liquid;
changing the volatiles content in the second liquid;
changing the second reactant concentration;
changing the average droplet size of the first liquid; and
a combination thereof.

33. A method as defined in claim 2, wherein the average droplet size of the second liquid is maintained at least adequately smaller than the average droplet size of the first liquid in a manner to decrease the probabilities of first droplets to collide with second droplets as compared to such probabilities when the average size of the second droplets is substantially the same as the average size of the first droplets.

34. A method as defined in claim 19, wherein the average droplet size of the second liquid is maintained at least adequately smaller than the average droplet size of the first liquid in a manner to decrease the probabilities of first droplets to collide with second droplets as compared to such probabilities when the average size of the second droplets is substantially the same as the average size of the first droplets.

* * * * *